(12) United States Patent
Weismantel et al.

(10) Patent No.: US 8,669,410 B2
(45) Date of Patent: Mar. 11, 2014

(54) FLUID-ABSORBENT ARTICLES

(75) Inventors: Matthias Weismantel, Jossgrund-Oberndorf (DE); Rüdiger Funk, Niedernhausen (DE); Ulrich Schröder, Frankenthal (DE); Marco Krüger, Mannheim (DE); John Joseph Louden, Manchester (GB)

(73) Assignee: BASF SE, Ludwigshafen (DE)

( * ) Notice: Subject to any disclaimer, the term of this patent is extended or adjusted under 35 U.S.C. 154(b) by 432 days.

(21) Appl. No.: 13/054,627

(22) PCT Filed: Jul. 30, 2009

(86) PCT No.: PCT/EP2009/059865
§ 371 (c)(1),
(2), (4) Date: Jan. 18, 2011

(87) PCT Pub. No.: WO2010/015561
PCT Pub. Date: Feb. 11, 2010

(65) Prior Publication Data
US 2011/0125119 A1    May 26, 2011

Related U.S. Application Data

(60) Provisional application No. 61/086,638, filed on Aug. 6, 2008.

(51) Int. Cl.
*A61F 13/15* (2006.01)

(52) U.S. Cl.
USPC ........... 604/367; 604/366; 604/368; 604/374; 604/375; 604/378

(58) Field of Classification Search
USPC .................. 604/367, 366, 368, 374, 375, 378
See application file for complete search history.

(56) References Cited

U.S. PATENT DOCUMENTS

| | | | |
|---|---|---|---|
| 5,269,980 A | | 12/1993 | Levendis et al. |
| 5,294,478 A | | 3/1994 | Wanek et al. |
| 2002/0007166 A1 | | 1/2002 | Mitchell et al. |
| 2005/0153123 A1 | * | 7/2005 | Herfert et al. ................ 428/327 |
| 2006/0004336 A1 | * | 1/2006 | Zhang et al. ................ 604/368 |
| 2006/0020250 A1 | | 1/2006 | Chester et al. |
| 2006/0134384 A1 | * | 6/2006 | Vinson et al. ................ 428/153 |
| 2006/0217508 A1 | | 9/2006 | Schmid et al. |
| 2007/0100115 A1 | | 5/2007 | Schmid et al. |
| 2008/0188586 A1 | | 8/2008 | Bruhns et al. |
| 2008/0188821 A1 | | 8/2008 | Losch et al. |
| 2009/0192035 A1 | | 7/2009 | Stueven et al. |
| 2009/0239071 A1 | | 9/2009 | Stueven et al. |
| 2009/0258994 A1 | | 10/2009 | Stueven et al. |
| 2010/0035059 A1 | | 2/2010 | Losch et al. |
| 2010/0062932 A1 | | 3/2010 | Losch et al. |
| 2010/0068520 A1 | | 3/2010 | Stueven |

FOREIGN PATENT DOCUMENTS

| | | |
|---|---|---|
| DE | 103 14 466 A1 | 10/2004 |
| DE | 103 40 253 A1 | 3/2005 |
| DE | 10 2004 024 437 A1 | 12/2005 |
| DE | 102005002412 A1 | 7/2006 |
| EP | 348 180 A2 | 12/1989 |
| JP | 2003252722 A | 9/2003 |
| WO | WO-96/40427 A1 | 12/1996 |
| WO | WO-9964084 | 12/1999 |
| WO | WO-0115649 A1 | 3/2001 |
| WO | WO-2006/014031 A1 | 2/2006 |
| WO | WO-2006/079631 A1 | 8/2006 |
| WO | WO-2008/009580 | 1/2008 |
| WO | WO-2008/009598 A1 | 1/2008 |
| WO | WO-2008/009599 A1 | 1/2008 |
| WO | WO-2008/009612 A1 | 1/2008 |
| WO | WO-2008/095892 | 8/2008 |
| WO | WO-2008095901 | 8/2008 |

OTHER PUBLICATIONS

Buchholz, Fredric L., et al.. *Modern Superabsorbent Polymer Technology*, "Commercial Processes for the Manufacture of Superabsorbent Polymers," pp. 71-103. New York: John Wiley & Sons, Inc., 1998.
International Search Report in International Application No. PCT/EP2009/059865 dated Oct. 22, 2009.

* cited by examiner

Primary Examiner — Jacqueline F. Stephens
(74) Attorney, Agent, or Firm — Marshall, Gerstein & Borun LLP

(57) ABSTRACT

The present invention relates to fluid-absorbent articles, comprising an upper liquid-pervious layer, a lower liquid-impervious layer, a fluid-absorbent core, wherein the fluid-absorbent core comprises a fibrous material and 10 to 95% by weight of spherical fluid-absorbent polymer particles, and an acquisition distribution layer, wherein the acquisition distribution layer comprises a fibrous material and 0 to 20% by weight of spherical fluid-absorbent polymer particles.

13 Claims, No Drawings

FLUID-ABSORBENT ARTICLES

CROSS-REFERENCE TO RELATED APPLICATIONS

This is the U.S. national phase of International Application No. PCT/EP2009/059865, filed Jul. 30, 2009, which claims the benefit of U.S. provisional patent Application No. 61/086,638, filed Aug. 6, 2008, incorporated herein in its entirety by reference.

The present invention relates to fluid-absorbent articles, comprising an upper liquid-pervious layer, a lower liquid-impervious layer, a fluid-absorbent core, wherein the fluid-absorbent core comprises a fibrous material and 10 to 95% by weight of spherical fluid-absorbent polymer particles, and an acquisition distribution layer, wherein the acquisition distribution layer comprises a fibrous material and 0 to 20% by weight of spherical fluid-absorbent polymer particles.

The preparation of fluid-absorbent polymers is described in the monograph "Modern Superabsorbent Polymer Technology", F. L. Buchholz and A. T. Graham, Wiley-VCH, 1998, on pages 71 to 103.

Fluid-absorbent articles are also described in the monograph "Modern Superabsorbent Polymer Technology" on pages 252 to 258.

The preparation of spherical fluid-absorbent polymer particles by polymerizing droplets of a monomer solution is described, for example, in EP 0 348 180 A1, WO 96/40427 A1, U.S. Pat. No. 5,269,980, DE 103 14 466 A1, DE 103 40 253 A1, DE 10 2004 024 437 A1, DE 10 2005 002 412 A1, DE 10 2006 001 596 A1, WO 2008/009580 A1, WO 2008/009598 A1, WO 2008/009599 A1 and WO 2008/009612 A1, and also the prior PCT applications PCT/EP2008/051336 and PCT/EP2008/051353.

Polymerization of monomer solution droplets in a gas phase surrounding the droplets ("dropletization polymerization") affords round fluid-absorbent polymer particles of high mean sphericity (mSPHT). The mean sphericity is a measure of the roundness of the polymer particles and can be determined, for example, with the Camsizer® image analysis system (Retsch Technology GmbH; Haan; Germany). The fluid-absorbent polymer particles obtained by dropletization polymerization are typically hollow spheres.

It was an object of the present invention to provide fluid-absorbent articles with improved properties, i.e. rewet value and acquisition time.

The object is achieved by fluid-absorbent articles, comprising
  (A) an upper liquid-pervious layer,
  (B) a lower liquid-impervious layer,
  (C) a fluid-absorbent core between the layer (A) and the layer (B), comprising a fibrous material and 10 to 95% by weight of fluid-absorbent polymer particles, and,
  (D) an acquisition distribution layer between the layer (A) and the core (C), comprising a fibrous material and 0 to 20% by weight of fluid-absorbent polymer particles,
wherein the fluid-absorbent polymer particles have a mean sphericity of at least 0.84.

The fluid-absorbent core (C) comprises of a fibrous material and preferably 20 to 80% by weight, more preferably 25 to 70% by weight, most preferably 30 to 60% by weight, of fluid-absorbent polymer particles.

The acquisition distribution layer (D) comprises of a fibrous material and preferably 0.01 to 15% by weight, more preferably 0.5 to 10% by weight, most preferably 1 to 5% by weight, of fluid-absorbent polymer particles.

The fluid-absorbent polymer particles useable for the inventive fluid-absorbent articles have a mean sphericity of preferably at least 0.86, more preferably at least 0.88 and most preferably at least 0.9. The sphericity (SPHT) is defined as $$SPHT = \frac{4\pi A}{U^2},$$

where A is the cross-sectional area and U is the cross-sectional circumference of the polymer particles. The mean sphericity is the volume-average sphericity.

The mean sphericity can be determined, for example, with the Camsizer® image analysis system (Retsch Technology GmbH; Haan; Germany):

For the measurement, the product is introduced through a funnel and conveyed to the falling shaft with a metering channel. While the particles fall past a light wall, they are recorded selectively by a camera. The images recorded are evaluated by the software in accordance with the parameters selected.

To characterize the roundness, the parameters designated as sphericity in the program are employed. The parameters reported are the mean volume-weighted sphericities, the volume of the particles being determined via the equivalent diameter $xc_{min}$. To determine the equivalent diameter $xc_{min}$, the longest chord diameter for a total of 32 different spatial directions is measured in each case. The equivalent diameter $xc_{min}$ is the shortest of these 32 chord diameters. To record the particles, the so-called CCD-zoom camera (CAM-Z) is used. To control the metering channel, a surface coverage fraction in the detection window of the camera (transmission) of 0.5% is predefined.

Fluid-absorbent polymer particles with relatively low sphericity are obtained by reverse suspension polymerization when the polymer beads are agglomerated during or after the polymerization.

The fluid-absorbent polymer particles prepared by customary solution polymerization (gel polymerization) are ground and classified after drying to obtain irregular polymer particles. The mean sphericity of these polymer particles is between approx. 0.72 and approx. 0.78.

The fluid-absorbent polymer particles useable for the inventive fluid-absorbent articles have a content of hydrophobic solvent of preferably less than 0.005% by weight, more preferably less than 0.002% by weight and most preferably less than 0.001% by weight. The content of hydrophobic solvent can be determined by gas chromatography, fair example by means of the headspace technique.

Fluid-absorbent polymer particles which have been obtained by reverse suspension polymerization still comprise typically approx. 0.01% by weight of the hydrophobic solvent used as the reaction medium.

The fluid-absorbent polymer particles useable for the inventive fluid-absorbent articles have a dispersant content of typically less than 1% by weight, preferably less than 0.5% by weight, more preferably less than 0.1% by weight and most preferably less than 0.05% by weight.

Fluid-absorbent polymer particles which have been obtained by reverse suspension polymerization still comprise typically at least 1% by weight of the dispersant, i.e. ethylcellulose, used to stabilize the suspension.

The fluid-absorbent polymer particles useable for the inventive fluid-absorbent articles have a moisture content of preferably at least 8% by weight, more preferably at least 10% by weight, most preferably at least 12% by weight.

The fluid-absorbent core (C) contains preferably at least 9 g, more preferably at least 10 g, most preferably at least 12 g, of the fluid-absorbent polymer particles.

The fluid-absorbent polymer particles useable for the fluid-absorbent articles according to the invention have a centrifuge retention capacity (CRC) of typically at least 10 g/g, preferably at least 15 g/g, preferentially at least 20 g/g, more preferably at least 25 g/g, most preferably at least 30 g/g. The centrifuge retention capacity (CRC) of the fluid-absorbent polymer particles is typically less than 50 g/g.

The fluid-absorbent polymer particles useable for the fluid-absorbent articles according to the invention have a saline flow conductivity (SFC) of typically at least $5 \times 10^{-7}$ cm$^3$ s/g, preferably at least $15 \times 10^{-7}$ cm$^3$ s/g, preferably at least $35 \times 10^{-7}$ cm$^3$ s/g, more preferably at least $120 \times 10^{-7}$ cm$^3$ s/g, most preferably at least $200 \times 10^{-7}$ cm$^3$ s/g. The saline flow conductivity (SFC) of the fluid-absorbent polymer particles is typically less than $500 \times 10^{-7}$ cm$^3$ s/g.

In a preferred embodiment of the present invention, the fluid-absorbent core comprises of 10 to 50% by weight of fluid-absorbent polymer particles having a centrifuge retention capacity (CRC) from 32 to 60 g/g.

In an other preferred embodiment of the present invention, the fluid-absorbent core comprises of 40 to 80% by weight of fluid-absorbent polymer particles having a saline flow conductivity (SFC) from 35 to $100 \times 10^{-7}$ cm$^3$ s/g.

In an other preferred embodiment of the present invention, the fluid-absorbent core comprises of 55 to 95% by weight of fluid-absorbent polymer particles having a saline flow conductivity (SFC) from 50 to $150 \times 10^{-7}$ cm$^3$ s/g.

DETAILED DESCRIPTION OF THE INVENTION

A. Definitions

As used herein, the term "fluid-absorbent composition" refers to a component of the fluid-absorbent article which is primarily responsible for the fluid handling of the fluid-absorbent article including acquisition, transport, distribution and storage of body fluids.

As used herein, the term "fluid-absorbent core" refers to a fluid-absorbent composition comprising a fibrous material and fluid-absorbent polymer particles. The fluid-absorbent core is primarily responsible for the fluid handling of the fluid-absorbent article including acquisition, transport, distribution and storage of body fluids.

As used herein, the term "layer" refers to a fluid-absorbent composition whose primary dimension is along its length and width. It should be known that the term "layer" is not necessarily limited to single layers or sheets of the fluid-absorbent composition. Thus a layer can comprise laminates, composites, combinations of several sheets or webs of different materials.

As used herein, the term "x-dimension" refers to the length, and the term "y-dimension" refers to the width of the fluid-absorbent composition, layer, core or article. Generally, the term "x-y dimension" refers to the plane, orthogonal to the height or thickness of the fluid-absorbent composition, layer, core or article.

As used herein, the term "z-dimension" refers to the dimension orthogonal to the length and width of the fluid-absorbent composition, layer, core or article. Generally, the term "z-dimension" refers to the height of the fluid-absorbent composition.

As used herein, the term "chassis" refers to fluid-absorbent material comprising the upper liquid-pervious layer and the lower liquid-impervious layer.

As used herein, the term "basis weight" indicates the weight of the fluid-absorbent core per square meter and it includes the chassis of the fluid-absorbent article. The basis weight is determined at discrete regions of the fluid-absorbent core: the front overall average is the basis weight of the fluid-absorbent core 5.5 cm forward of the center of the core to the front distal edge of the core; the insult zone is the basis weight of the fluid-absorbent core 5.5 cm forward and 0.5 cm backwards of the center of the core; the back overall average is the basis weight of the fluid-absorbent core 0.5 cm backward of the center of the core to the rear distal edge of the core.

As used herein, the term "density" indicates the weight of the fluid-absorbent core per volume and it includes the chassis of the fluid-absorbent article. The density is determined at discrete regions of the fluid-absorbent core: the front overall average is the density of the fluid-absorbent core 5.5 cm forward of the center of the core to the front distal edge of the core; the insult zone is the density of the fluid-absorbent core 5.5 cm forward and 0.5 cm backwards of the center of the core; the back overall average is the density of the fluid-absorbent core 0.5 cm backward of the center of the core to the rear distal edge of the core.

Further, it should be understood, that the term "upper" refers to fluid-absorbent compositions which are nearer to the wearer of the fluid-absorbent article. Generally, the topsheet is the nearest composition to the wearer of the fluid-absorbent article, hereinafter described as "upper liquid-pervious layer". Contrarily, the term "lower" refers to fluid-absorbent compositions which are away from the wearer of the fluid-absorbent article. Generally, the backsheet is the composition which is furthermost away from the wearer of the fluid-absorbent article, hereinafter described as "lower liquid-impervious layer".

As used herein, the term "liquid-pervious" refers to a substrate, layer or a laminate thus permitting liquids, i.e. body fluids such as urine, menses and/or vaginal fluids to readily penetrate through its thickness.

As used herein, the term "liquid-impervious" refers to a substrate, layer or a laminate that does not allow body fluids to pass through in a direction generally perpendicular to the plane of the layer at the point of liquid contact under ordinary use conditions.

Fluid-absorbent articles comprising more than one fluid-absorbent core, in a preferred manner comprising a double-core system including an upper core and a lower core, hereinafter called "primary core" and "secondary core".

As used herein, the term "hydrophilic" refers to the wettability of fibers by water deposited on these fibers. The term "hydrophilic" is defined by the contact angle and surface tension of the body fluids. According to the definition of Robert F. Gould in the 1964 American Chemical Society publication "Contact angle, wettability and adhesion", a fiber is referred to as hydrophilic, when the contact angle between the liquid and the fiber, especially the fiber surface, is less than 90° or when the liquid tends to spread spontaneously on the same surface.

Contrarily, term "hydrophobic" refers to fibers showing a contact angle of greater than 90° or no spontaneously spreading of the liquid across the surface of the fiber.

As used herein, the term "section" or "zone" refers to a definite region of the fluid-absorbent composition.

As used herein, the term "article" refers to any three-dimensional solid material being able to acquire and store fluids discharged from the body. Preferred articles according to the present invention are disposable fluid-absorbent articles that are designed to be worn in contact with the body of a user such as disposable fluid-absorbent pantiliners, sanitary napkins, catameniials, incontinence inserts/pads, diapers, training pant diapers, breast pads, interlabial inserts/pads and the like.

As used herein, the term "body fluids" refers to any fluid produced and discharged by human or animal body, such as urine, menstrual fluids, feces, vaginal secretions and the like.

B. Fluid-Absorbent Polymer Particles

The fluid-absorbent polymer particles are preferably prepared by polymerizing droplets of a monomer solution comprising
a) at least one ethylenically unsaturated, acid group-bearing monomer which may be at least partly neutralized,
b) at least one crosslinker,
c) at least one initiator,
d) optionally one or more ethylenically unsaturated monomers copolymerizable with the monomers mentioned under a),
e) optionally one or more water-soluble polymers and
f) water,
in a gas phase surrounding the droplets, wherein the polymerization in the droplet taking place in homogeneous phase.

The fluid-absorbent polymer particles are typically insoluble in water.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids such as styrenesulfonic acid and 2-acrylamido-2-methylpropanesulfonic acid (AMPS).

Impurities may have a strong impact on the polymerization. Preference is given to especially purified monomers a). Useful purification methods are disclosed in WO 2002/055469 A1, WO 2003/078378 A1 and WO 2004/035514 A1. A suitable monomer a) is according to WO 2004/035514 A1 purified acrylic acid having 99.8460% by weight of acrylic acid, 0.0950% by weight of acetic acid, 0.0332% by weight of water, 0.0203 by weight of propionic acid, 0.0001% by weight of furfurals, 0.0001% by weight of maleic anhydride, 0.0003% by weight of diacrylic acid and 0.0050% by weight of hydroquinone monomethyl ether.

The content of acrylic acid and/or salts thereof in the total amount of monomers a) is preferably at least 50 mol %, more preferably at least 90 mol %, most preferably at least 95 mol %.

The acid groups of the monomers a) are typically partly neutralized, preferably to an extent of from 25 to 85 mol %, preferentially to an extent of from 50 to 80 mol %, more preferably from 60 to 75 mol %, for which the customary neutralizing agents can be used, preferably alkali metal hydroxides, alkali metal oxides, alkali metal carbonates or alkali metal hydrogen carbonates, and mixtures thereof. Instead of alkali metal salts, it is also possible to use ammonia. Sodium and potassium are particularly preferred as alkali metals, but very particular preference is given to sodium hydroxide, sodium carbonate or sodium hydrogen carbonate, and mixtures thereof. Typically, the neutralization is achieved by mixing in the neutralizing agent as an aqueous solution, as a melt or preferably also as a solid. For example, sodium hydroxide with a water content significantly below 50% by weight may be present as a waxy material having a melting point above 23° C. In this case, metered addition as piece material or melt at elevated temperature is possible.

The monomers a) comprise typically polymerization inhibitors, preferably hydroquinone monoethers, as inhibitor for storage.

The monomer solution comprises preferably up to 250 ppm by weight, more preferably not more than 130 ppm by weight, most preferably not more than 70 ppm by weight, preferably not less than 10 ppm by weight, more preferably not less than 30 ppm by weight and especially about 50 ppm by weight of hydroquinone monoether, based in each case on acrylic acid, with acrylic acid salts being counted as acrylic acid. For example, the monomer solution can be prepared using acrylic acid having an appropriate hydroquinone monoether content.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized by a free-radical mechanism into the polymer chain and functional groups which can form covalent bonds with the acid groups of monomer a). In addition, polyvalent metal ions which can form coordinate bond with at least two acid groups of monomer a) are also suitable crosslinkers b).

The crosslinkers b) are preferably compounds having at least two free-radically polymerizable groups which can be polymerized by a free-radical mechanism into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and in DE: 103 31 450 A1, mixed acrylates which, as well as acrylate groups, comprise further ethylenically unsaturated groups, as described in DE 103 314 56 A1 and DE: 103 55 401 A1, or crosslinker mixtures, as described, for example, in DE: 195 43 368, DE-A-196 46 484 A1, WO 90/15830 A1 and WO 2002/32962 A2.

Suitable crosslinkers b) are in particular pentaerythritol triallyl ether, tetraallyloxyethane, N,N'-methylenebisacrylamide, 15-tuply ethoxylated trimethylolpropane, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol and especially the triacrylate of 3-tuply ethoxylated glycerol.

The amount of crosslinker b) is preferably from 0.05 to 1.5% by weight, more preferably from 0.1 to 1% by weight, most preferably from 0.3 to 0.6% by weight, based in each case on monomer a). On increasing the amount of crosslinker b) the centrifuge retention capacity (CRC) decreases and the absorption under a pressure of 21.0 g/cm² (AUL) passes through a maximum.

The initiators c) used may be all compounds which disintegrate into free radicals under the polymerization conditions, for example peroxides, hydroperoxides, hydrogen peroxide, persulfates, azo compounds and redox initiators. Preference is given to the use of water-soluble initiators. In some cases, it is advantageous to use mixtures of various initiators, for example mixtures of hydrogen peroxide and sodium or potassium peroxodisulfate. Mixtures of hydrogen peroxide and sodium peroxodisulfate can be used in any proportion.

Particularly preferred initiators c) are azo initiators such as 2,2"-azobis[2-(2-imidazolin-2-yl)propane] dihydrochloride and 2,2'-azobis[2-(5-methyl-2-imidazolin-2-yl)propane]dihydrochloride, and photoinitiators such as 2-hydroxy-2-methylpropiophenone and 1-[4-(2-hydroxyethoxy)phenyl]-2-hydroxy-2-methyl-1-propan-1-one, redox initiators such as sodium persulfate/hydroxymethylsulfinic acid, ammonium peroxodisulfate/hydroxymethylsulfinic acid, hydrogen peroxide/hydroxymethylsulfinic acid, sodium persulfate/ascorbic acid, ammonium peroxodisulfate/ascorbic acid and hydrogen peroxide/ascorbic acid, photoinitiators such as 1-[4-(2-hydroxyethoxy)phenyl]-2-hydroxy-2-methyl-1-propan-1-one, and mixtures thereof.

The initiators are used in customary amounts, for example in amounts of from 0.001 to 5% by weight, preferably from 0.01 to 2% by weight, based on the monomers a).

Examples of ethylenically unsaturated monomers c) which are copolymerizable with the monomers a) are acrylamide, methacrylamide, hydroxyethyl acrylate, hydroxyethyl methacrylate, dimethylaminoethyl acrylate, dimethylaminoethyl methacrylate, dimethylaminopropyl acrylate and diethylaminopropyl methacrylate.

Useful water-soluble polymers d) include polyvinyl alcohol, polyvinylpyrrolidone, starch, starch derivatives, modified cellulose such as methylcellulose or hydroxyethylcellulose, gelatin, polyglycols or polyacrylic acids, preferably starch, starch derivatives and modified cellulose.

For optimal action, the preferred polymerization inhibitors require dissolved oxygen. Therefore, the monomer solution can be freed of dissolved oxygen before the polymerization by inertization, i.e. flowing through with an inert gas, preferably nitrogen. The oxygen content of the monomer solution is preferably lowered before the polymerization to less than 1 ppm by weight, more preferably to less than 0.5 ppm by weight.

The solids content of the monomer solution is preferably at least 35% by weight, preferentially at least 38% by weight, more preferably at least 40% by weight, most preferably at least 42% by weight. The solids content is the sum of all constituents which are involatile after the polymerization.

The polymerization inhibitors can also be removed by absorption, for example on activated carbon.

The monomer solution is metered into the gas phase to form droplets. The droplets can be generated, for example, by means of a dropletizer plate.

A dropletizer plate is a plate having at least one bore, the liquid entering the bore from the top. The dropletizer plate or the liquid can be oscillated, which generates a chain of ideally monodisperse droplets at each bore on the underside of the dropletizer plate. In a preferred embodiment, the dropletizer plate is not agitated.

The number and size of the bores are selected according to the desired capacity and droplet size. The droplet diameter is typically 1.9 times the diameter of the bore. What is important here is that the liquid to be dropletized does not pass through the bore too rapidly and the pressure drop over the bore is not too great. Otherwise, the liquid is not dropletized, but rather the liquid jet is broken up (sprayed) owing to the high kinetic energy. The Reynolds number based on the throughput per bore and the bore diameter is preferably less than 2000, preferentially less than 1000, more preferably less than 500 and most preferably less than 250.

The dropletizer plate has typically at least one bore, preferably at least 10, more preferably at least 50 and typically up to 10 000 bores, preferably up to 5000, more preferably up to 1000 bores, the bores typically being distributed uniformly over the dropletizer plate, preferably in so-called triangular pitch, i.e. three bores in each case form the corners of an equilateral triangle. The diameter of the bores is adjusted to the desired droplet size.

However, the droplets can also be generated by means of pneumatic drawing dies, rotation, cutting of a jet or rapidly actuable microvalve dies.

In a pneumatic drawing die, a liquid jet together with a gas stream is accelerated through a diaphragm. The gas rate can be used to influence the diameter of the liquid jet and hence the droplet diameter.

In the case of droplet generation by rotation, the liquid passes through the orifices of a rotating disk. As a result of the centrifugal force acting on the liquid, droplets of defined size are torn off. Preferred apparatus for rotary dropletization are described, for example, in DE 43 08 842 A1.

The emerging liquid jet can also be cut into defined segments by means of a rotating blade or an air-jet. Each segment then forms a droplet.

In the case of use of microvalve dies, droplets with defined liquid volume are generated directly.

The droplets generated have a mean diameter of preferably at least 200 µm, more preferably of at least 250 µm and most preferably of at least 300 µm, the droplet diameter being determinable by means of light scattering and meaning the volume-average mean diameter.

The mean diameter of the fluid-absorbent polymer particles obtainable by the process is preferably at least 200 µm, more preferably from 250 to 600 µm, very particularly from 300 to 500 µm, the particle diameter being determinable by light scattering and meaning the volume-average mean diameter. 90% of the polymer particles have a diameter of preferably from 100 to 800 µm, more preferably from 150 to 700 µm and most preferably from 200 to 600 µm.

The polymerization reactor is flowed through by a gas. The carrier gas can be conducted through the reaction chamber in concurrent or in countercurrent to the free-falling droplets of the monomer solution, preferably in concurrent, i.e. from the bottom upward. After one pass, the carrier gas is preferably recycled at least partly, preferably to an extent of at least 50%, more preferably to an extent of at least 75%, into the reaction chamber as cycle gas. Typically, a portion of the carrier gas is discharged after each pass, preferably up to 10%, more preferably up to 3% and most preferably up to 1%.

The gas velocity is preferably adjusted such that the flow in the polymerization reactor is directed, for example no convection currents opposed to the general flow direction are present, and is, for example, from 0.01 to 5 m/s, preferably from 0.02 to 4 m/s, more preferably from 0.05 to 3 m/s, most preferably from 0.1 to 2 m/s.

The gas flowing through the reactor is appropriately preheated to the reaction temperature upstream of the reactor.

The gas entrance temperature, i.e. the temperature with which the gas enters the reaction chamber, is preferably from 160 to 250° C., more preferably from 180 to 230° C., most preferably from 190 to 220° C.

Advantageously, the gas entrance temperature is controlled in such a way that the gas exit temperature, i.e. the temperature with which the gas leaves the reaction chamber, is from 100 to 180° C., more preferably from 110 to 160° C., most preferably from 120 to 140° C.

The reaction can be carried out under elevated pressure or under reduced pressure; preference is given to a reduced pressure of up to 100 mbar relative to ambient pressure.

The reaction offgas, i.e. the gas leaving the reaction chamber, may, for example, be cooled in a heat exchanger. This condenses water and unconverted monomer a). The reaction offgas can then be reheated at least partly and recycled into the reactor as cycle gas. A portion of the reaction offgas can be discharged and replaced by fresh gas, in which case water and unconverted monomers a) present in the reaction offgas can be removed and recycled.

Particular preference is given to a thermally integrated system, i.e. a portion of the waste heat in the cooling of the offgas is used to heat the cycle gas.

The reactors can be trace-heated. In this case, the trace heating is adjusted such that the wall temperature is at least 5° C. above the internal reactor temperature and condensation on the reactor walls is reliably prevented.

The fluid-absorbent polymer particles prepared by dropletization polymerization have a moisture content of preferably at least 10% by weight, more preferably at least 12% by weight, most preferably at least 14% by weight. The moisture content can be adjusted by the polymerization temperature and the residence time.

In a preferred embodiment of the present invention residual monomers in the fluid-absorbent polymer particles obtained by dropletization polymerization are removed by a thermal aftertreatment in a fluidized state in the presence of a gas stream. The residual monomers can be removed better at relatively high temperatures and relatively long residence times. What is important here is that the fluid-absorbent polymer particles are not too dry. In the case of excessively dry particles, the residual monomers decrease only insignificantly. Too high a water content increases the caking tendency of the fluid-absorbent polymer particles. In order that the fluid-absorbent polymer particles do not dry too rapidly during the thermal aftertreatment, the gas flowing in shall already comprise steam.

The polymer particles can subsequently be postcrosslinked for further improvement of the properties.

Postcrosslinkers are compounds which comprise groups which can form at least two covalent bonds with the carboxylate groups of the polymer particles. Suitable compounds are, for example, polyfunctional amines, polyfunctional amidoamines, polyfunctional epoxides, as described in EP 0 083 022 A2, EP 0 543 303 A1 and EP 0 937 736 A2, di- or polyfunctional alcohols as described in DE 33 14 019 A1, DE 35 23 617 A1 and EP 0 450 922 A2, or β-hydroxyalkylamides, as described in DE 102 04 938 A1 and U.S. Pat. No. 6,239,230.

In addition, DE 40 20 780 C1 describes cyclic carbonates, DE 198 07 502 A1 describes 2-oxazolidone and its derivatives such as 2-hydroxyethyl-2-oxazolidone, DE 198 07 992 C1 describes bis- and poly-2-oxazolidinones, DE 198 54 573 A1 describes 2-oxotetrahydro-1,3-oxazine and its derivatives, DE 198 54 574 A1 describes N-acyl-2-oxazolidones, DE 102 04 937 A1 describes cyclic ureas, DE 103 34 584 A1 describes bicyclic amide acetals, EP 1 199 327 A2 describes oxetanes and cyclic ureas, and WO 2003/31482 A1 describes morpholine-2,3-dione and its derivatives, as suitable postcrosslinkers.

Particularly preferred postcrosslinkers are ethylene carbonate, mixtures of propylene glycol and 1,4-butanediol, ethylene glycol diglycidyl ether and reaction products of polyamides and epichlorohydrin.

Very particularly preferred postcrosslinkers are 2-hydroxyethyl-2-oxazolidone, 2-oxazolidone and 1,3-propanediol.

In addition, it is also possible to use postcrosslinkers which comprise additional polymerizable ethylenically unsaturated groups, as described in DE 37 13 601 A1.

The amount of postcrosslinker is preferably from 0.001 to 2% by weight, more preferably from 0.02 to 1% by weight, most preferably from 0.05 to 0.2% by weight, based in each case on the polymer.

In a preferred embodiment of the present invention, polyvalent cations are applied to the particle surface in addition to the postcrosslinkers before, during or after the postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate and lactate. Aluminum sulfate is preferred. Apart from metal salts, it is also possible to use polyamines and/or polymeric amines as polyvalent cations.

The amount of polyvalent cation used is, for example, from 0.001 to 1.5% by weight, preferably from 0.005 to 1% by weight, more preferably from 0.02 to 0.8% by weight, based in each case on the polymer.

The postcrosslinking is typically performed in such a way that a solution of the postcrosslinker is sprayed onto the hydrogel or the dry polymer particles. After the spraying, the polymer particles coated with the postcrosslinker are dried thermally, and the postcrosslinking reaction can take place either before or during the drying.

The spraying of a solution of the postcrosslinker is preferably performed in mixers with moving mixing tools, such as screw mixers, disk mixers, plowshare mixers and paddle mixers. Particular preference is given to horizontal mixers such as plowshare mixers and paddle mixers, very particular preference to vertical mixers. Suitable mixers are, for example, Lödige mixers, Bepex mixers, Nauta mixers, Processall mixers and Schugi mixers. The postcrosslinker solution can also be sprayed into a fluidized bed.

The postcrosslinkers are typically used as an aqueous solution. The addition of nonaqueous solvent can be used to adjust the penetration depth of the postcrosslinker into the polymer particles.

The thermal drying is preferably carried out in contact dryers, more preferably paddle dryers, most preferably disk dryers. Suitable dryers are, for example, Bepex dryers and Nara dryers. Moreover, it is also possible to use fluidized bed dryers.

The drying can be effected in the mixer itself, by heating the jacket or blowing in warm air. Equally suitable is a downstream dryer, for example a shelf dryer, a rotary tube oven or a heatable screw. It is particularly advantageous to mix and dry in a fluidized bed dryer.

Preferred drying temperatures are in the range from 100 to 250° C., preferably from 120 to 220° C., more preferably from 130 to 210° C., most preferably from 150 to 200° C. The preferred residence time at this temperature in the reaction mixer or dryer is preferably at least 10 minutes, more preferably at least 20 minutes, most preferably at least 30 minutes, and typically at most 60 minutes.

To further improve the properties, the postcrosslinked polymer particles can be coated or subsequently moistened. Suitable coatings for improving the acquisition behavior and the saline flow conductivity (SFC) are, for example, inorganic inert substances, such as water-insoluble metal salts, organic polymers, cationic polymers and di- or polyvalent metal cations. Suitable coatings for dust binding are, for example, polyols. Suitable coatings against the undesired caking tendency of the polymer particles are, for example, fumed silica, such as Aerosil® 200, and surfactants, such as Span® 20.

C. Fluid-Absorbent Articles

The fluid-absorbent article comprises of
(A) an upper liquid-pervious layer
(B) a lower liquid-impervious layer
(C) a fluid-absorbent core between (A) and (B) comprising
    from 5 to 90% by weight a fibrous material and from 10 to 95% by weight fluid-absorbent polymer particles;
    preferably from 20 to 80% by weight a fibrous material and from 20 to 80% by weight fluid-absorbent polymer particles;
    more preferably from 30 to 75% by weight a fibrous material and from 25 to 70% by weight fluid-absorbent polymer particles;
    most preferably from 40 to 70% by weight a fibrous material and from 30 to 60% by weight fluid-absorbent polymer particles;
(D) an acquisition-distribution layer between (A) and (C), comprising
    from 80 to 100% by weight a fibrous material and from 0 to 20% by weight fluid-absorbent polymer particles;
    preferably from 85 to 99.9% by weight a fibrous material and from 0.01 to 15% by weight fluid-absorbent polymer particles;
    more preferably from 90 to 99.5% by weight a fibrous material and from 0.5 to 10% by weight fluid-absorbent polymer particles;
    most preferably from 95 to 99% by weight a fibrous material and from 1 to 5% by weight fluid-absorbent polymer particles;
(E) an optional tissue layer disposed immediately above and/or below (C); and
(F) other optional components.

Fluid-absorbent articles are understood to mean, for example, incontinence pads and incontinence briefs for adults or diapers for babies. Suitable fluid-absorbent articles including fluid-absorbent compositions comprising fibrous materials and optionally fluid-absorbent polymer particles to form fibrous webs or matrices for the substrates, layers, sheets and/or the fluid-absorbent core.

Suitable fluid-absorbent articles are composed of several layers whose individual elements must show preferably definite functional parameter such as dryness for the upper liquid-pervious layer, vapor permeability without wetting through for the lower liquid-impervious layer, a flexible, vapor permeable and thin fluid-absorbent core, showing fast absorption rates and being able to retain highest quantities of body fluids, and an acquisition-distribution layer between the upper layer and the core, acting as transport and distribution layer of the discharged body fluids. These individual elements are combined such that the resultant fluid-absorbent article meets overall criteria such as flexibility, water vapour breathability, dryness, wearing comfort and protection on the one side, and concerning liquid retention, rewet and prevention of wet through on the other side. The specific combination of these layers provides a fluid-absorbent article delivering both high protection levels as well as high comfort to the consumer.

Liquid-Pervious Layer (A)

The liquid-pervious layer (A) is the layer which is in direct contact with the skin. Thus, the liquid-pervious layer is preferably compliant, soft feeling and non-irritating to the consumer's skin. Generally, the term "liquid-pervious" is understood thus permitting liquids, i.e. body fluids such as urine, menses and/or vaginal fluids to readily penetrate through its thickness. The principle function of the liquid-pervious layer is the acquisition and transport of body fluids from the wearer towards the fluid-absorbent core. Typically liquid-pervious layers are formed from any materials known in the art such as nonwoven material, films or combinations thereof. Suitable liquid-pervious layers (A) consist of customary synthetic or semisynthetic fibers or bicomponent fibers or films of polyester, polyolefins, rayon or natural fibers or any combinations thereof. In the case of nonwoven materials, the fibers should generally be bound by binders such as polyacrylates. Additionally the liquid-pervious layer may contain elastic compositions thus showing elastic characteristics allowing to be stretched in one or two directions.

Suitable synthetic fibers are made from polyvinyl chloride, polyvinyl fluoride, polytetrafluorethylene, polyvinylidene chloride, polyacrylics, polyvinyl acetate, polyethylvinyl acetate, non-soluble or soluble polyvinyl alcohol, polyolefins such as polyethylene, polypropylene, polyamides, polyesters, polyurethanes, polystyrenes and the like.

Examples for films are apertured formed thermoplastic films, apertured plastic films, hydroformed thermoplastic films, reticulated thermoplastic films, porous foams, reticulated foams, and thermoplastic scrims.

Examples of suitable modified or unmodified natural fibers include cotton, bagasse, kemp, flax, silk, wool, wood pulp, chemically modified wood pulp, jute, rayon, ethyl cellulose, and cellulose acetate.

Suitable wood pulp fibers can be obtained by chemical processes such as the Kraft and sulfite processes, as well as from mechanical processes, such as ground wood, refiner mechanical, thermo-mechanical, chemi-mechanical and chemi-thermo-mechanical pulp processes. Further, recycled wood pulp fibers, bleached, unbleached, elementally chlorine free (ECF) or total chlorine free (TCF) wood pulp fibers can be used.

The fibrous material may comprise only natural fibers or synthetic fibers or any combination thereof. Preferred materials are polyester, rayon and blends thereof, polyethylene, and polypropylene.

The fibrous material as a component of the fluid-absorbent compositions may be hydrophilic, hydrophobic or can be a combination of both hydrophilic and hydrophobic fibers. The definition of hydrophilic is given in the section "definitions" in the chapter above. The selection of the ratio hydrophilic/hydrophobic and accordingly the amount of hydrophilic and hydrophobic fibers within fluid-absorbent composition will depend upon fluid handling properties and the amount of fluid-absorbent polymer particles of the resulting fluid-absorbent composition. Such, the use of hydrophobic fibers is preferred if the fluid-absorbent composition is adjacent to the wearer of the fluid-absorbent article, that is to be used to replace partially or completely the upper liquid-pervious layer, preferably formed from hydrophobic nonwoven materials. Hydrophobic fibers can also be member of the lower breathable, but fluid-impervious layer, acting there as a fluid-impervious barrier.

Examples for hydrophilic fibers are cellulosic fibers, modified cellulosic fibers, rayon, polyester fibers such as polyethylen terephthalate, hydrophilic nylon and the like. Hydrophilic fibers can also be obtained from hydrophobic fibers which are hydrophilized by e.g. surfactant-treating or silica-treating. Thus, hydrophilic thermoplastic fibers derived from polyolefins such as polypropylene, polyamides, polystyrenes or the like by surfactant-treating or silica-treating.

To increase the strength and the integrity of the upper-layer, the fibers should generally show bonding sites, which act as crosslinks between the fibers within the layer.

Technologies for consolidating fibers in a web are mechanical bonding, thermal bonding and chemical bonding. In the process of mechanical bonding the fibers are entangled mechanically, e.g., by water jets (spunlace) to give integrity to the web. Thermal bonding is carried out by means of rising the temperature in the presence of low-melting polymers. Examples for thermal bonding processes are spunbonding, through-air bonding and resin bonding.

Preferred means of increasing the integrity are thermal bonding, spunbonding, resin bonding, through-air bonding and/or spunlace.

In the case of thermal bonding, thermoplastic material is added to the fibers. Upon thermal treatment at least a portion of this thermoplastic material is melting and migrates to intersections of the fibers caused by capillary effects. These intersections solidify to bond sites after cooling and increase the integrity of the fibrous matrix. Moreover, in the case of chemically stiffened cellulosic fibers, melting and migration of the thermoplastic material has the effect of increasing the pore size of the resultant fibrous layer while maintaining its density and basis weight. Upon wetting, the structure and integrity of the layer remains stable. In summary, the addition of thermoplastic material leads to improved fluid permeability of discharged body fluids and thus to improved acquisition properties.

Suitable thermoplastic materials including polyolefins such as polyethylene and polypropylene, polyesters, copolyesters, polyvinyl acetate, polyethylvinyl acetate, polyvinyl chloride, polyvinylidene chloride, polyacrylics, polyamides, copolyamides, polystyrenes, polyurethanes and copolymers of any of the mentioned polymers.

Suitable thermoplastic fibers can be made from a single polymer that is a monocomponent fiber. Alternatively, they can be made from more than one polymer, e.g., bi-component or multicomponent fibers. The term "bicomponent fibers" refers to thermoplastic fibers that comprise a core fiber made from a different fiber material than the shell. Typically, both fiber materials have different melting points, wherein generally the sheath melts at lower temperatures. Bi-component fibers can be concentric or eccentric depending whether the sheath has a thickness that is even or uneven through the cross-sectional area of the bi-component fiber. Advantage is given for eccentric bi-component fibers showing a higher compressive strength at lower fiber thickness. Further bi-component fibers can show the feature "uncrimped" (unbent) or "crimped" (bent), further bi-component fibers can demonstrate differing aspects of surface lubricity.

Examples of bi-component fibers include the following polymer combinations: polyethylene/polypropylene, polyethylvinyl acetate/polypropylene, polyethylene/polyester, polypropylene/polyester, copolyester/polyester and the like.

Suitable thermoplastic materials have a melting point of lower temperatures that will damage the fibers of the layer; but not lower than temperatures, where usually the fluid-absorbent articles are stored. Preferably the melting point is between about 75° C. and 175° C. The typical length of thermoplastic fibers is from about 0.4 to 6 cm, preferably from about 0.5 to 1 cm. The diameter of thermoplastic fibers is defined in terms of either denier (grams per 9000 meters) or dtex (grams per 10 000 meters). Typical thermoplastic fibers have a dtex in the range from about 1.2 to 20, preferably from about 1.4 to 10.

A further mean of increasing the integrity of the fluid-absorbent composition is the spunbonding technology. The nature of the production of fibrous layers by means of spunbonding is based on the direct spinning of polymeric granulates into continuous filaments and subsequently manufacturing the fibrous layer.

Spunbond fabrics are produced by depositing extruded, spun fibers onto a moving belt in a uniform random manner followed by thermal bonding the fibers. The fibers are separated during the web laying process by air jets. Fiber bonds are generated by applying heated rolls or hot needles to partially melt the polymer and fuse the fibers together. Since molecular orientation increases the melting point, fibers that are not highly drawn can be used as thermal binding fibers. Polyethylene or random ethylene/propylene copolymers are used as low melting bonding sites.

Besides spunbonding, the technology of resin bonding also belongs to thermal bonding subjects. Using this technology to generate bonding sites, specific adhesives, based on e.g. epoxy, polyurethane and acrylic are added to the fibrous material and the resulting matrix is thermically treated. Thus the web is bonded with resin and/or thermal plastic resins dispersed within the fibrous material.

As a further thermal bonding technology through-air bonding involves the application of hot air to the surface of the fibrous fabric. The hot air is circulated just above the fibrous fabric, but does not push through the fibrous fabric. Bonding sites are generated by the addition of binders. Suitable binders used in through-air thermal bonding include crystalline binder fibers, bi-component binder fibers, and powders. When using crystalline binder fibers or powders, the binder melts entirely and forms molten droplets throughout the nonwoven's cross-section. Bonding occurs at these points upon cooling. In the case of sheath/core binder fibers, the sheath is the binder and the core is the carrier fiber. Products manufactured using through-air ovens tend to be bulky, open, soft, strong, extensible, breathable and absorbent. Through-air bonding followed by immediate cold calendering results in a thickness between a hot roll calendered product and one that has been though-air bonded without compression. Even after cold calendering, this product is softer, more flexible and more extensible than area-bond hot-calendered material.

Spunlacing ("hydroentangiement") is a further method of increasing the integrity of a web. The formed web of loose fibers (usually air-laid or wet-laid) is first compacted and prewetted to eliminate air pockets. The technology of spunlacing uses multiple rows of fine high-speed jets of water to strike the web on a porous belt or moving perforated or patterned screen so that the fibers knot about one another. The water pressure generally increases from the first to the last injectors. Pressures as high as 150 bar are used to direct the water jets onto the web. This pressure is sufficient for most of the non-woven fibers, although higher pressures are used in specialized applications.

The spunlace process is a nonwovens manufacturing system that employs jets of water to entangle fibers and thereby provide fabric integrity. Softness, drape, conformability, and relatively high strength are the major characteristics of spunlace non-woven.

In newest researches benefits are found in some structural features of the resulting liquid-pervious layers. For example, the thickness of the layer is very important and influences together with its x-y dimension the acquisition-distribution behaviour of the layer. If there is further some profiled structure integrated, the acquisition-distribution behaviour can be directed depending on the three-dimensional structure of the layer. Thus 3D-polyethylene in the function of liquid-pervious layer is preferred.

Thus, suitable liquid-pervious layers (A) are nonwoven layers formed from the fibers above by thermal bonding, spunbonding, resin bonding or through-air bonding. Further suitable liquid-pervious layers are 3D-polyethylene layers and spunlace.

Preferably the 3D-polyethylene layers and spunlace show basis weights from 12 to 22 gsm.

Typically liquid-pervious layers (A) extend partially or wholly across the fluid-absorbent structure and can extend into and/or form part of all the preferred sideflaps, side wrapping elements, wings and ears.

Liquid-Impervious Layer (B)

The liquid-impervious layer (B) prevents the exudates absorbed and retained by the fluid-absorbent core from wetting articles which are in contact with the fluid-absorbent article, as for example bedsheets, pants, pajamas and undergarments. The liquid-impervious layer (B) may thus comprise a woven or a nonwoven material, polymeric films such as thermoplastic film of polyethylene or polypropylene, or composite materials such as film-coated nonwoven material.

Suitable liquid-impervious layers include nonwoven, plastics and/or laminates of plastic and nonwoven. Both, the plastics and/or laminates of plastic and nonwoven may appropriately be breathable, that is, the liquid-impervious layer (B) can permit vapors to escape from the fluid-absorbent material. Thus the liquid-impervious layer has to have a definite water vapor transmission rate and at the same time the level of impermeability. To combine these features, suitable liquid-impervious layers including at least two layers, e.g. laminates from fibrous nonwoven having a specified basis weight and pore size, and a continuous three-dimensional film of e.g. polyvinylalcohol as the second layer having a specified thickness and optionally having pore structure. Such laminates acting as a barrier and showing no liquid transport or wet through. Thus, suitable liquid-impervious layers comprising at least a first breathable layer of a porous web which is a fibrous nonwoven, e.g. a composite web of a meltblown nonwoven layer or of a spun-bonded nonwoven layer made from synthetic fibers and at least a second layer of a resilient three dimensional web consisting of a liquid-impervious polymeric film, e.g. plastics optionally having pores acting as capillaries, which are preferably not perpendicular to the plane of the film but are disposed at an angle of less than 90° relative to the plane of the film.

Suitable liquid-impervious layers are permeable for vapor. Preferably the liquid-impervious layer is constructed from vapor permeable material showing a water vapor transmission rate (WVTR) of at least about 100 gsm per 24 hours, preferably at least about 250 gsm per 24 hours and most preferred at least about 500 gsm per 24 hours.

Preferably the liquid-impervious layer (B) is made of nonwoven comprising hydrophobic materials, e.g. synthetic fibers or a liquid-impervious polymeric film comprising plastics e.g. polyethylene. The thickness of the liquid-impervious layer is preferably 15 to 30 µm.

Further, the liquid-impervious layer (B) is preferably made of a laminate of non-woven and plastics comprising a nonwoven having a density of 12 to 15 gsm and a polyethylene layer having a thickness of about 10 to 20 µm.

The typically liquid-impervious layer (B) extends partially or wholly across the fluid-absorbent structure and can extend into and/or form part of all the preferred sideflaps, side wrapping elements, wings and ears.

Fluid-Absorbent Core (C)

The fluid-absorbent core (C) is disposed between the upper liquid-pervious layer (A) and the lower liquid-impervious layer (B). Suitable fluid-absorbent cores (C) may be selected from any of the fluid-absorbent core-systems known in the art provided that requirements such as vapor permeability, flexibility and thickness are met. Suitable fluid-absorbent cores refer to any fluid-absorbent composition whose primary function is to acquire, transport, distribute, absorb, store and retain discharged body fluids.

The top view area of the fluid-absorbent core (C) is preferably at least 200 $cm^2$, more preferably at least 2550 $cm^2$, most preferably at least 300 $cm^2$. The top view area is the part of the core that is face-to-face to the upper liquid-pervious layer.

According to the present invention the fluid-absorbent core can include the following components:
1. an optional core cover
2. a fluid storage layer
3. an optional dusting layer 1. Optional Core Cover In order to increase the integrity of the fluid-absorbent core, the core is provided with a cover. This cover may be at the top and/or at the bottom of the fluid-absorbent core. Further, this cover may include the whole fluid-absorbent core with a unitary sheet of material and thus function as a wrap. Wrapping is possible as a full wrap, a partial wrap or as a C-Wrap.

The material of the core cover may comprise any known type of substrate, including webs, garments, textiles, films, tissues and laminates of two or more substrates or webs. The core cover material may comprise natural fibers, such as cellulose, cotton, flax, linen, hemp, wool, silk, fur, hair and naturally occurring mineral fibers. The core cover material may also comprise synthetic fibers such as rayon and lyocell (derived from cellulose), polysaccharides (starch), polyolefin fibers (polypropylene, polyethylene), polyamides, polyester, butadiene-styrene block copolymers, polyurethane and combinations thereof. Preferably, the core cover comprises synthetic fibers or tissue.

The fibers may be mono- or multicomponent. Multicomponent fibers may comprise a homopolymer, a copolymer or blends thereof.

2. Fluid-Storage Layer

The fluid-absorbent compositions included in the fluid-absorbent core comprise fibrous materials and fluid-absorbent polymer particles.

Fibers useful in the present invention include natural fibers and synthetic fibers. Examples of suitable modified or unmodified natural fibers are given in the chapter "Liquid-pervious Layer (A)" above. From those, wood pulp fibers are preferred.

Examples of suitable synthetic fibers are given in the chapter "Liquid-pervious Layer (A)" above. The fibrous material may comprise only natural fibers or synthetic fibers or any combination thereof.

The fibrous material as a component of the fluid-absorbent compositions may be hydrophilic, hydrophobic or can be a combination of both hydrophilic and hydrophobic fibers.

Generally for the use in a fluid-absorbent core, which is the embedded between the upper layer (A) and the lower layer (B), hydrophilic fibers are preferred. This is especially the case for fluid-absorbent compositions that are desired to quickly acquire, transfer and distribute discharged body fluids to other regions of the fluid-absorbent composition or fluid-absorbent core. The use of hydrophilic fibers is especially preferred for fluid-absorbent compositions comprising fluid-absorbent polymer particles.

Examples for hydrophilic fibers are given in the chapter "Liquid-pervious Layer (A)" above. Preferably, the fluid-absorbent core is made from viscose acetate, polyester and/or polypropylene.

The fibrous material of the fluid-absorbent core may be uniformly mixed to generate a homogenous or inhomogeneous fluid-absorbent core. Alternatively the fibrous material may be concentrated or laid in separate layers optionally comprising fluid-absorbent polymer material. Suitable storage layers of the fluid-absorbent core comprising homogenous mixtures of fibrous materials comprising fluid-absorbent polymer material. Suitable storage layers of the fluid-absorbent core including a layered core-system comprise homogenous mixtures of fibrous materials and comprise fluid-absorbent polymer material, whereby each of the layers may be built from any fibrous material by means known in the art. The sequence of the layers may be directed such that a desired fluid acquisition, distribution and transfer results, depending on the amount and distribution of the inserted fluid-absorbent material, e.g. fluid-absorbent polymer particles. Preferably there are discrete zones of highest absorption rate or retention within the storage layer of the fluid-absorbent core, formed of layers or inhomogenous mixtures of the fibrous material, acting as a matrix for the incorporation of fluid-absorbent polymer particles. The zones may extend over the full area or may form only parts of the fluid-absorbent core.

Suitable fluid-absorbent cores comprise fibrous material and fluid-absorbent material. Suitable is any fluid-absorbent material that is capable of absorbing and retaining body fluids or body exudates such as cellulose wadding, modified and unmodified cellulose, crosslinked cellulose, laminates, composites, fluid-absorbent foams, materials described as in the chapter "Liquid-pervious Layer (A)" above, fluid-absorbent polymer particles and combinations thereof.

Typically the fluid-absorbent cores may contain a single type of fluid-absorbent polymer particles or may contain fluid-absorbent polymer particles derived from different kinds of fluid-absorbent polymer material. Thus, it is possible to add fluid-absorbent polymer particles from a single kind of polymer material or a mixture of fluid-absorbent polymer particles from different kinds of polymer materials, e.g. a mixture of regular fluid-absorbent polymer particles, derived from gel polymerization with fluid-absorbent polymer particles, derived from dropletization polymerization. Alternatively it is possible to add fluid-absorbent polymer particles derived from inverse suspension polymerization.

Alternatively it is possible to mix fluid-absorbent polymer particles showing different feature profiles. Thus, the fluid-absorbent core may contain fluid-absorbent polymer particles with uniform pH value, or it may contain fluid-absorbent polymer particles with different pH values, e.g. two- or more component mixtures from fluid-absorbent polymer particles with a pH in the range from about 4.0 to about 7.0. Preferably, applied mixtures deriving from mixtures of fluid-absorbent polymer particles got from gel polymerization or inverse suspension polymerization with a pH in the range from about 4.0 to about 7.0 and fluid-absorbent polymer particles got from drop polymerization.

Suitable fluid-absorbent cores are also manufactured from loose fibrous materials by adding fluid-absorbent particles and/or fluid-absorbent polymer fibers or mixtures thereof.

The fluid-absorbent polymer fibers may be formed from a single type of fluid-absorbent polymer fiber or may contain fluid-absorbent polymer fibers from different polymeric materials. The addition of fluid-absorbent polymer fibers may be preferred for being distributed and incorporated easily into the fibrous structure and remaining better in place than fluid-absorbent polymer particles. Thus, the tendency of gel blocking caused by contacting each other is reduced. Further, fluid-absorbent polymer fibers are softer and more flexible.

In the process of manufacturing the fluid-absorbent core, fluid-absorbent polymer particles and/or fluid-absorbent fibers are brought together with structure forming compounds such as fibrous matrices. Thus, the fluid-absorbent polymer particles and/or fluid-absorbent fibers may be added during the process of forming the fluid-absorbent core from loose fibers. The fluid-absorbent core may be formed by mixing fluid-absorbent polymer particles and/or fluid-absorbent fibers with fibrous materials of the matrix at the same time or adding one component to the mixture of two or more other components either at the same time or by continuously adding.

Suitable fluid-absorbent cores including mixtures of fluid-absorbent polymer particles and/or fluid-absorbent fibers and fibrous material building matrices for the incorporation of the fluid-absorbent material. Such mixtures can be formed homogenously, that is all components are mixed together to get a homogenous structure. The amount of the fluid-absorbent materials may be uniform throughout the fluid-absorbent core, or may vary, e.g. between the central region and the distal region to give a profiled core concerning the concentration of fluid-absorbent material.

Techniques of application of the fluid-absorbent polymer materials into the absorbent core are known to persons skilled in the art and may be volumetric, loss-in-weight or gravimetric. Known techniques include the application by vibrating systems, single and multiple auger systems, dosing roll, weigh belt, fluid bed volumetric systems and gravitational sprinkle and/or spray systems. Further techniques of insertion are falling dosage systems consensus and contradictory pneumatic application or vacuum printing method of applying the fluid absorbent polymer materials.

Suitable fluid-absorbent cores may also include layers, which are formed by the process of manufacturing the fluid-absorbent article. The layered structure may be formed by subsequently generating the different layers in z-direction.

Alternatively a core-structure can be formed from two or more preformed layers to get a layered fluid-absorbent core. The layers may have different concentrations of fluid-absorbent polymer material showing concentrations in the range from about 10 to 95%. These uniform or different layers can be fixed to each other at their adjacent plane surfaces. Alternatively, the layers may be combined in a way that a plurality of chambers are formed, in which separately fluid-absorbent polymer material is incorporated.

Suitable preformed layers are processed as e.g. air-laid, wet-laid, laminate or composite structure.

Alternatively layers of other materials can be added, e.g. layers of opened or closed celled foams or perforated films. Included are also laminates of at least two layers comprising said fluid-absorbent polymer material.

Further a composite structure can be formed from a carrier layer (e.g. a polymer film), onto which the fluid-absorbent polymer material is affixed. The fixation can be done at one side or at both sides. The carrier layer may be pervious or impervious for body-fluids.

Alternatively, it is possible to add monomer solution after the formation of a layer or onto a carrier layer and polymerize the coating solution by means of UV-induced polymerization technologies. Thus, "in situ"-polymerization is a further method for the application of fluid-absorbent polymers.

Thus, suitable fluid-absorbent cores comprising from 5 to 90% by weight a fibrous material and from 10 to 95% by weight fluid-absorbent polymer particles; preferably from 20 to 80% by weight a fibrous material and from 20 to 80% by weight fluid-absorbent polymer particles; more preferably from 30 to 75% by weight a fibrous material and from 25 to 70% by weight fluid-absorbent polymer particles and most preferably from 40 to 70% by weight a fibrous material and from 30 to 60% by weight fluid-absorbent polymer particles.

The quantity of fluid-absorbent polymer particles and/or fluid-absorbent fibers within the fluid-absorbent core is from 3 to 20 g, preferably from 6 to 14 g, and from 8 to 12 g in the case of maxi-diapers, and in the case of incontinence products up to about 50 g.

Typically fluid-absorbent articles comprising at least an upper liquid-pervious layer (A), at least a lower liquid-impervious layer (B) and at least one fluid-absorbent core between the layer (A) and the layer (B) besides other optional layers. In order to increase the control of body fluid absorption and/or to increase the flexibility in the ratio weight percentages of fluid-absorbent polymer particles to fibrous matrix it may be advantageous to add one or more further fluid-absorbent cores. The addition of a second fluid-absorbent core to the first fluid-absorbent core offers more possibilities in body fluid transfer and distribution. Moreover higher quantities of discharged body fluids can be retained. Having the opportunity of combining several layers showing different fluid-absorbent polymer concentration and content, it is possible to reduce the thickness of the fluid-absorbent article to a minimum even if there are several fluid-absorbent cores included.

Suitable fluid-absorbent cores may be formed from any material known in the art which is designed to acquire, transfer, and retain discharged body fluids. The technology of manufacturing may also be anyone known in the art. Preferred technologies include the application of monomer-solution to a transported fibrous matrix and thereby polymerizing, known as in-situ technology, or the manufacturing of air-laid composites.

Suitable fluid-absorbent articles are including single or multi-core systems in any combination with other layers which are typically found in fluid-absorbent articles. Preferred fluid-absorbent articles include single- or double-core systems; most preferably fluid-absorbent articles include a single fluid-absorbent core.

The fluid-absorbent core typically has a uniform size or profile. Suitable fluid-absorbent cores can also have profiled structures, concerning the shape of the core and/or the content of fluid-absorbent polymer particles and/or the distribution of the fluid-absorbent polymer particles and/or the dimensions of the different layers if a layered fluid-absorbent core is present.

It is known that absorbent cores providing a good wet immobilization by combining several layers, e.g. a substrate layer, layers of fluid-absorbent polymer and layers of thermoplastic material. Suitable absorbent cores may also comprise tissue or tissue laminates. Known in the art are single or double layer tissue laminates formed by folding the tissue or the tissue laminate onto itself.

These layers or foldings are preferably joined to each e.g. by addition of adhesives or by mechanical, thermal or ultrasonic bonding or combinations thereof. Fluid-absorbent polymer particles may be comprised within or between the individual layers, e.g. by forming separate fluid-absorbent polymer-layers.

Thus, according to the number of layers or the height of a voluminous core, the resulting thickness of the fluid-absorbent core will be determined. Thus, fluid-absorbent cores may be flat as one layer (plateau) or have three-dimensional profile.

Generally the upper liquid-pervious layer (A) and the lower liquid-impervious layer (B) may be shaped and sized according to the requirements of the various types of fluid-absorbent articles and to accommodate various wearer's sizes. Thus, the combination of the upper liquid-pervious layer and the lower liquid-impervious layer may have all dimensions or shapes known in the art. Suitable combinations have an hourglass shape, rectangular shape, trapezoidal shape, t- or double t-shape or showing anatomical dimensions.

The fluid-absorbent core may comprise additional additives typically present in fluid-absorbent articles known in the art. Exemplary additives are fibers for reinforcing and stabilizing the fluid-absorbent core. Preferably polyethylene is used for reinforcing the fluid-absorbent core.

Further suitable stabilizer for reinforcing the fluid-absorbent core are materials acting as binder.

In varying the kind of binder material or the amount of binder used in different regions of the fluid-absorbent core it is possible to get a profiled stabilization. For example, different binder materials exhibiting different melting temperatures may be used in regions of the fluid-absorbent core, e.g. the lower melting one in the central region of the core, and the higher melting in the distal regions. Suitable binder materials may be adhesive or non-adhesive fibers, continuously or discontinuously extruded fibers, bi-component staple fibers, nonelastomeric fibers and sprayed liquid binder or any combination of these binder materials.

Further, thermoplastic compositions usually are added to increase the integrity of the core layer. Thermoplastic compositions may comprise a single type of thermoplastic polymers or a blend of thermoplastic polymers. Alternatively, the thermoplastic composition may comprise hot melt adhesives comprising at least one thermoplastic polymer together with thermoplastic diluents such as tackifiers, plasticizers or other additives, e.g. antioxidants. The thermoplastic composition may further comprise pressure sensitive hot melt adhesives comprising e.g. crystalline polypropylene and an amorphous polyalphaolefin or styrene block copolymer and mixture of waxes.

Suitable thermoplastic polymers are styrenic block copolymers including A-B-A triblock segments, A-B diblock segments and $(A-B)_n$ radial block copolymer segments. The letter A designs non-elastomeric polymer segments, e.g. polystyrene, and B stands for unsaturated conjugated diene or their (partly) hydrogenated form. Preferably B comprises isoprene, butadiene, ethylene/butylene (hydrogenated butadiene), ethylene/propylene (hydrogenated isoprene) and mixtures thereof.

Other suitable thermoplastic polymers are amorphous polyolefins, amorphous polyalphaolefins and metallocene polyolefins.

Concerning odor control, perfumes and/or odor control additives are optionally added. Suitable odor control additives are all substances of reducing odor developed in carrying fluid-absorbent articles over time known in the art. Thus, suitable odor control additives are inorganic materials, such as zeolites, activated carbon, bentonite, silica, aerosile, kieselguhr, clay; chelants such as ethylenediamine tetraacetic acid (EDTA), cyclodextrins, aminopolycarbonic acids, ethylenediamine tetramethylene phosphonic acid, aminophosphate, polyfunctional aromates, N,N-disuccinic acid.

Suitable odor control additives are further antimicrobial agents such as quaternary ammonium, phenolic, amide and nitro compounds and mixtures thereof; bactericides such as silver salts, zinc salts, cetylpyridinium chloride and/or triclosan as well as surfactants having an HLB value of less than 12.

Suitable odor control additives are further compounds with anhydride groups such as maleic-, itaconic-, polymaleic- or polyitaconic anhydride, copolymers of maleic acid with $C_2$-$C_8$ olefins or styrene, polymaleic anhydride or copolymers of maleic anhydride with isobutene, di-isobutene or styrene, compounds with acid groups such as ascorbic, benzoic, citric, salicylic or sorbic acid and fluid-soluble polymers of monomers with acid groups, homo- or co-polymers of $C_3$-$C_5$ mono-unsaturated carboxylic acids.

Suitable odor control additives are further perfumes such as allyl caproate, allyl cyclohexaneacetate, allyl cyclohexanepropionate, allyl heptanoate, amyl acetate, amyl propionate, anethol, anixic aldehyde, anisole, benzaldehyde, benzyl acetete, benzyl acetone, benzyl alcohole, benzyl butyrate, benzyl formate, camphene, camphor gum, laevo-carveol, cinnamyl formate, cis-jasmone, citral, citronellol and its derivatives, cuminic alcohol and its derivatives, cyclal C, dimethyl benzyl carbinol and its derivatives, dimethyl octanol and its derivatives, eucalyptol, geranyl derivatives, lavandulyl acetete, ligustral, d-limonene, linalool, linalyl derivatives, menthone and its derivatives, myrcene and its derivatives, neral, nerol, p-cresol, p-cymene, orange terpenes, alpha-ponene, 4-terpineol, thymol etc.

Masking agents are also used as odor control additives. Masking agents are in solid wall material encapsulated perfumes. Preferably, the wall material comprises a fluid-soluble cellular matrix which is used for time-delay release of the perfume ingredient.

Further suitable odor control additives are transition metals such as Cu, Ag, Zn; enzymes such as urease-inhibitors, starch, pH buffering material, chitin, green tea plant extracts, ion exchange resin, carbonate, bicarbonate, phosphate, sulfate or mixtures thereof.

Preferred odor control additives are green tea plant extracts, silica, zeolite, carbon, starch, chelating agent, pH buffering material, chitin, kieselguhr, clay, ion exchange resin, carbonate, bicarbonate, phosphate, sulfate, masking agent or mixtures thereof. Suitable concentrations of odor control additives are from about 0.5 to about 300 gsm.

Newest developments propose the addition of wetness indication additives. Besides electrical monitoring the wetness in the fluid-absorbent article, wetness indication additives comprising a hot melt adhesive with a wetness indicator are known. The wetness indication additive changes the colour from yellow to a relatively dark and deep blue. This colour change is readily perceivable through the liquid-impervious outer material of the fluid-absorbent article. Existing wetness indication is also achieved via application of water soluble ink patterned on the backsheet which disappears when wet.

Suitable wetness indication additives comprising a mixture of sorbitan monooleate and polyethoxylated hydrogenated castor oil. Preferably, the amount of the wetness indication additive is in the range of about 1 to 5% by weight related to the weight of the fluid-absorbent core.

The basis weight of the fluid-absorbent core is in the range of 600 to 1200 gsm. The density of the fluid-absorbent core is in the range of 0.1 to 0.25 g/cm$^3$. The thickness of the fluid-absorbent core is in the case of diapers in the range of 1 to 5 mm, preferably 1.5 to 3 mm, in the case of incontinence products in the range of 3 to 15 mm.

3. Optional Dusting Layer

An optional component for inclusion into the absorbent core is a dusting layer adjacent to. The dusting layer is a fibrous layer and may be placed on the top and/or the bottom of the absorbent core. Typically, the dusting layer is underlying the storage layer. This underlying layer is referred to as a dusting layer, since it serves as carrier for deposited fluid-absorbent polymer particles during the manufacturing process of the fluid-absorbent core. If the fluid-absorbent polymer material is in the form of macrostructures, films or flakes, the insertion of a dusting layer is not necessary. In the case of fluid-absorbent polymer particles derived from dropletization polymerization, the particles have a smooth surface with no edges. Also in this case, the addition of a dusting layer to the fluid-absorbent core is not necessary. On the other side, as a great advantage the dusting layer provides some additional fluid-handling properties such as wicking performance and may offer reduced incidence of pin-holing and or pock marking of the liquid impervious layer (B).

Preferably, the dusting layer is a fibrous layer comprising fluff (cellulose fibers).

Acquisition-Distribution Layer (D)

An acquisition-distribution layer (D) is located between the upper layer (A) and the fluid-absorbent core (C) and is preferably constructed to efficiently acquire discharged body fluids and to transfer and distribute them to other regions of the fluid-absorbent composition or to other layers, where the body fluids are immobilized and stored. Thus, the upper layer transfers the discharged liquid to the acquisition-distribution layer (D) for distributing it to the fluid-absorbent core.

The acquisition-distribution layer comprises fibrous material and optionally fluid-absorbent polymer particles.

The fibrous material may be hydrophilic, hydrophobic or can be a combination of both hydrophilic and hydrophobic fibers. It may be derived from natural fibers, synthetic fibers or a combination of both.

Suitable acquisition-distribution layers are formed from cellulosic fibers and/or modified cellulosic fibers and/or synthetics or combinations thereof. Thus, suitable acquisition-distribution layers may contain cellulosic fibers, in particular wood pulp fluff. Examples of further suitable hydrophilic, hydrophobic fibers, as well as modified or unmodified natural fibers are given in the chapter "Liquid-pervious Layer (A)" above.

Especially for providing both fluid acquisition and distribution properties, the use of modified cellulosic fibers is preferred. Examples for modified cellulosic fibers are chemically treated cellulosic fibers, especially chemically stiffened cellulosic fibers. The term "chemically stiffened cellulosic fibers" means cellulosic fibers that have been stiffened by chemical means to increase the stiffness of the fibers. Such means include the addition of chemical stiffening agent in the form of coatings and impregnates. Suitable polymeric stiffening agents can include: cationic modified starches having nitrogen-containing groups, latexes, wet strength resins such as polyamide-epichlorohydrin resin, polyacrylamide, urea formaldehyde and melamine formaldehyde resins and polyethylenimine resins.

Stiffening may also include altering the chemical structure, e.g. by crosslinking polymer chains. Thus crosslinking agents can be applied to the fibers that are caused to chemically form intrafiber crosslink bonds. Further cellulosic fibers may be stiffened by crosslink bonds in individualized form. Suitable chemical stiffening agents are typically monomeric crosslinking agents including $C_2$-$C_8$ dialdehyde, $C_2$-$C_8$ monoaldehyde having an acid functionality, and especially $C_2$-$C_9$ polycarboxylic acids.

Preferably the modified cellulosic fibers are chemically treated cellulosic fibers. Especially preferred are curly fibers which can be obtained by treating cellulosic fibers with citric acid. Preferably the basis weight of cellulosic fibers and modified cellulosic fibers is from 50 to 200 gsm.

Suitable acquisition-distribution layers further include synthetical fibers. Known examples of synthetical fibers are found in the Chapter "Liquid-pervious Layer (A)" above. 3D-polyethylene in the function of acquisition-distribution layer is preferred.

Further, as in the case of cellulosic fibers, hydrophilic synthetical fibers are preferred. Hydrophilic synthetical fibers may be obtained by chemical modification of hydrophobic fibers. Preferably, hydrophilization is carried out by surfactant treatment of hydrophobic fibers. Thus the surface of the hydrophobic fiber can be rendered hydrophilic by treatment with a nonionic or ionic surfactant, e.g., by spraying the fiber with a surfactant or by dipping the fiber into a surfactant. Further preferred are permanent hydrophilic synthetic fibers.

The fibrous material of the acquisition-distribution layer may be fixed to increase the strength and the integrity of the layer. Technologies for consolidating fibers in a web are mechanical bonding, thermal bonding and chemical bonding. Detailed description of the different methods of increasing the integrity of the web is given in the Chapter "Liquid-pervious Layer (A)" above.

Preferred acquisition-distribution layers comprise fibrous material and fluid-absorbent polymer particles distributed within. The fluid-absorbent polymer particles may be added during the process of forming the layer from loose fibers, or, alternatively, it is possible to add monomer solution after the formation of the layer and polymerize the coating solution by means of UV-induced polymerisation technologies. Thus, "in situ"-polymerisation is a further method for the application of fluid-absorbent polymers.

Thus, suitable acquisition-distribution layers comprising from 80 to 100% by weight a fibrous material and from 0 to 20% by weight fluid-absorbent polymer particles; preferably from 85 to 99.9% by weight a fibrous material and from 0.1 to 15% by weight fluid-absorbent polymer particles; more preferably from 90 to 99.5% by weight a fibrous material and from 0.5 to 10% by weight fluid-absorbent polymer particles; and most preferably from 95 to 99% by weight a fibrous material and from 1 to 5% by weight fluid-absorbent polymer particles.

Preferred acquisition-distribution layers show basis weights in the range from 20 to 200 gsm, most preferred in the range from 40 to 50 gsm, depending on the concentration of fluid-absorbent polymer particles.

Optional Tissue Layer (E)

An optional tissue layer is disposed immediately above and/or below (C).

The material of the tissue layer may comprise any known type of substrate, including webs, garments, textiles and films. The tissue layer may comprise natural fibers, such as cellulose, cotton, flax, linen, hemp, wool, silk, fur, hair and naturally occurring mineral fibers. The tissue layer may also comprise synthetic fibers such as rayon and lyocell (derived from cellulose), polysaccharides (starch), polyolefin fibers (polypropylene, polyethylene), polyamides, polyester, butadiene-styrene block copolymers, polyurethane and combinations thereof. Preferably, the tissue layer comprises cellulose fibers.

Other Optional Components (F)

1. Leg Cuff

Typical leg cuffs comprising nonwoven materials which can be formed by direct extrusion processes during which the fibers and the nonwoven materials are formed at the same time, or by laying processes of preformed fibers which can be laid into non-woven materials at a later point of time. Examples for direct extrusion processes include spunbonding, meltblowing, solvent spinning, electrospinning and combinations thereof. Examples of laying processes include wet-laying and dry-laying (e.g. air-laying, carding) methods. Combinations of the processes above include spunbond-meltblown-spunbond (sms), spunbond-meltblow-meltblown-spunbond (smms), spunbond-carded (sc), spunbond-airlaid (sa), meltblown-airlaid (ma) and combinations thereof. The combinations including direct extrusion can be combined at the same point in time or at a subsequent point in time. In the examples above, one or more individual layers can be produced by each process. Thus, "sms" means a three layer nonwoven material, "smsms" or "ssmms" means a five layer nonwoven material. Usually, small type letters (sms) designate individual layers, whereas capital letters (SMS) designate the compilation of similar adjacent layers.

Further, suitable leg cuffs are provided with elastic strands.

Preferred are leg cuffs from synthetic fibers showing the layer combinations sms, smms or smsms. Preferred are nonwovens with the density of 13 to 17 gsm. Preferably leg cuffs are provided with two elastic strands.

2. Elastics

The elastics are used for securely holding and flexibly closing the fluid-absorbent article around the wearers body, e.g. the waist and the legs to improve containment and fit. Leg elastics are placed between the outer and inner layers or the fluid-absorbent article, or between the outer cover and the bodyside liner. Suitable elastics comprising sheets, ribbons or strands of thermoplastic polyurethane, elastomeric materials, poly(ether-amide) block copolymers, thermoplastic rubbers, styrene-butadiene copolymers, silicon rubbers, natural rubbers, synthetic rubbers, styrene isoprene copolymers, styrene ethylene butylene copolymers, nylon copolymers, spandex fibers comprising segmented polyurethane and/or ethylene-vinyl acetate copolymer. The elastics may be secured to a substrate after being stretched, or secured to a stretched substrate. Otherwise, the elastics may be secured to a substrate and then elastisized or shrunk, e.g. by the application of heat.

3. Closing System

The closing system include tape tabs, landing zone, elastomerics, pull ups and the belt system.

At least a part of the first waist region is attached to a part of the second waist region by the closing system to hold the fluid-absorbent article in place and to form leg openings and the waist of the fluid-absorbent article. Preferably the fluid-absorbent article is provided with a re-closable closing system.

The closing system is either re-sealable or permanent, including any material suitable for such a use, e.g. plastics, elastics, films, foams, nonwoven substrates, woven substrates, paper, tissue, laminates, fiber reinforced plastics and the like, or combinations thereof. Preferably the closing system includes flexible materials and works smooth and softly without irritating the wearer's skin.

One part of the closing elements is an adhesive tape, or comprises a pair of laterally extending tabs disposed on the lateral edges of the first waist region. Tape tabs are typically attached to the front body panel and extend laterally from each corner of the first waistband. These tape tabs include an adhesive inwardly facing surface which is typically protected prior to use by a thin, removable cover sheet.

Suitable tape tabs may be formed of thermoplastic polymers such as polyethylene, polyurethane, polystyrene, poly-carbonate, polyester, ethylene vinyl acetate, ethylene vinyl alcohol, ethylene vinyl acetate acrylate or ethylene acrylic acid copolymers.

Suitable closing systems comprise further a hook portion of a hook and loop fastener and the target devices comprise the loop portion of a hook and loop fastener.

Suitable mechanical closing systems including a landing zone. Mechanical closing systems may fasten directly into the outer cover. The landing zone may act as an area of the fluid-absorbent article into which it is desirable to engage the tape tabs. The landing zone may include a base material and a plurality of tape tabs. The tape tabs may be embedded in the base material of the landing zone. The base material may include a loop material. The loop material may include a backing material and a layer of a non-woven spunbond web attacked to the backing material.

Thus suitable landing zones can be made by spunbonding. Spunbonded nonwoven are made from melt-spun fibers formed by extruding molten thermoplastic material. Preferred is bioriented polypropylene (BOPP), or brushed/closed loop in the case of mechanical closing systems.

Further, suitable mechanical closing systems including elastic units serving as a flexible waist band for fluid-absorbents articles, such as pants or pull-ups. The elastic units enabling the fluid-absorbent article to be pulled down by the wearer as e.g. a training pant.

Suitable pants-shaped fluid-absorbent article has front section, rear section, crotch section, side sections for connecting the front and rear sections in lateral direction, hip section, elastic waist region and liquid-tight outer layer. The hip section is arranged around the waist of the user. The disposable pants-shaped fluid-absorbent article (pull-up) has favorable flexibility, stretchability, leak-proof property and fit property, hence imparts excellent comfort to the wearer.

Suitable pull-ups comprising thermoplastic films, sheets and laminates having a low modulus, good tear strength and high elastic recovery.

Suitable closing systems may further comprise elastomerics for the production of elastic areas within the fastening devices of the fluid-absorbent article. Elastomerics provide a conformable fit of the fluid-absorbent article to the wearer at the waist and leg openings, while maintaining adequate performance against leakage.

Suitable elastomerics are elastomeric polymers or elastic adhesive materials showing vapor permeability and liquid barrier properties. Preferred elastomerics are retractable after elongation to a length equivalent to its original length.

Suitable closing systems further comprise a belt system, comprising waist-belt and leg-belts for flexibly securing the fluid-absorbent article on the body of the wearer and to provide an improved fit on the wearer. Suitable waist-belts comprising two elastic belts, a left elastic belt, and a right elastic belt. The left elastic belt is associated with each of the left angular edges. The right elastic belt associated with each of the right angular edges. The left and right side belts are elastically extended when the absorbent garment is laid flat. Each belt is connected to and extends between the front and rear of the fluid-absorbent article to form a waist hole and leg holes.

Preferably the belt system is made of elastomerics, thus providing a conformable fit of the fluid-absorbent article and maintaining adequate performance against leakage.

D. Fluid-Absorbent Article Construction

The present invention further relates to the joining of the components and layers, films, sheets, tissues or substrates mentioned above to provide the fluid-absorbent article. At least two, preferably all layers, films, sheets, tissues or substrates are joined.

Suitable fluid-absorbent articles include a single- or multiple fluid-absorbent core-system. Preferably fluid-absorbent articles include a single- or double fluid-absorbent core-system.

Suitable fluid-storage layers of the fluid-absorbent core comprising homogenous or inhomogeneous mixtures of fibrous materials comprising fluid-absorbent polymer particles homogenously or inhomogeneously dispersed in it. Suitable fluid-storage layers of the fluid-absorbent core including a layered fluid-absorbent core-system comprising homogenous mixtures of fibrous materials and optionally comprising fluid-absorbent polymer particles, whereby each of the layers may be prepared from any fibrous material by means known in the art.

In order to immobilize the fluid-absorbent polymer particles, the adjacent layers are fixed by the means of thermoplastic materials, thereby building connections throughout the whole surface or alternatively in discrete areas of junction. For the latter case, cavities or pockets are built carrying the fluid-absorbent particles. The areas of junction may have a regular or irregular pattern, e.g. aligned with the longitudinal axis of the fluid-absorbent core or in a pattern of polygons, e.g. pentagons or hexagons. The areas of junction itself may be of rectangular, circular or squared shape with diameters between about 0.5 mm and 2 mm. Fluid-absorbent articles comprising areas of junction show a better wet strength.

The construction of the products chassis and the components contained therein is made and controlled by the discrete application of hotmelt adhesives as known to people skilled in the art. Examples would be e.g. Dispomelt 505B, Dispomelt Cool 1101, as well as other specific function adhesives manufactured by National Starch or Henkel.

In order to describe the present invention in detail, embodiments are generated which are described hereinafter.

Thus, preferred fluid-absorbent articles are subsequently described in detail.

Embodiment 1

One preferred embodiment of the present invention is described in Embodiment 1 hereinafter. Thus, a preferred fluid-absorbent article comprising
- (A) an upper liquid-pervious layer comprising a spunbond layer (three piece coverstock);
- (B) a lower liquid-impervious layer comprising a composite of breathable polyethylene film and spunbond nonwoven;
- (C) a single fluid-absorbent core between (A) and (B) comprising between 10 to 50% by weight fluid-absorbent polymer particles based on the total absorbent core weight and including a multi-layered fluid-storage section comprising the following sequence:
  1. a homogenous upper core fluff layer of hydrophilic fibrous matrix of wood pulp fibers (cellulose fibers) containing about 50% of the total fluff amount;
  2. a fluid-absorbent layer comprising fluid-absorbent polymer particles; suitable fluid-absorbent polymer particles for such construction having a centrifuge retention capacity (CRC) from about 32 to 60 g/g;
  3. a homogenous lower core fluff layer of hydrophilic fibrous matrix of wood pulp fibers (cellulose fibers) containing about 50% of the total fluff amount and acting as a dusting layer; and (D) an air-through bonded acquisition-distribution layer between (A) and (C) having a basis weight of 30 to 80 gsm; the acquisition-distribution layer is rectangular shaped and smaller than the fluid-absorbent core having a size of about 150 to about 250 cm².

The construction of the products chassis and the components contained therein is made and controlled by the discrete application of hotmelt adhesives as known to people skilled in the art. Examples would be e.g. Dispomelt 505B, Dispomelt Cool 1101, as well as other specific function adhesives manufactured by National Starch or Henkel.

Ultra-thin high-loaded fluid-absorbent layers can be formed by immobilization of fluid-absorbent polymer particles on a non-woven sheet using hotmelt adhesives. Preferably the fluid-absorbent polymer particles form longitudinal strips or discrete spots. Other patterns of the fluid-absorbent polymer particles are also possible.

In a preferred embodiment the ultra-thin high-loaded fluid-absorbent layers comprise at least two sheets comprising immobilized fluid-absorbent polymer particles.

Examples of ultra-thin high-loaded fluid-absorbent layers are described in EP 1 293 187 A1, U.S. Pat. No. 6,972,011, EP 1 447 066 A1, EP 1 447 067 A1, EP 1 609 448 A1, JP 2004/313580, US 2005/0137085, US 2006/0004336, US 2007/0135785 WO 2008/155699 A1, WO 2008/155701 A2, WO 2008/155702 A1, WO 2008/155710 A1, WO 2008/155711 A1, WO 2004/071363 A1, US 2003/0181115, WO 2005/097025, US 2007/156108, US 2008/0125735, and WO 2008/155722 A2, which explicitly forms part of the present disclosure.

Construction Example of Embodiment 1

The fluid-absorbent core consists of a multi-layered single core system each layer having a uniform rectangular size. The layered fluid-absorbent core between (A) and (B) comprises a multi-layered system of hydrophilic fibers (cellulose fibers, fluff pulp fibers). The total fluff pulp weight is 20.45 g divided equally between upper core (1) and lower core (3). The density of the fluid-absorbent core is for the front overall average 0.18 g/cm³, for the insult zone 0.17 g/cm³, for the back overall average 0.15 g/cm³. The basis weight of the fluid-absorbent core is for the front overall average 802.75 gsm, for the insult zone 825.94 gsm, for the back overall average 766.14 gsm.

Fluid-absorbent layer (2) holds 31.38% by weight distributed fluid-absorbent polymer particles, the quantity of fluid-absorbent polymer particles within the fluid-absorbent core is 9.34 g.

The fluid-absorbent polymer particles derived from dropletization polymerization as described in WO 2008/009580 A1, table 1, example 2, exhibiting the following features and absorption profile:
CRC of 37.2 g/g
SFC of $10 \times 10^{-7}$ cm³ s/g
AUHL of 28.1 g/g
AUL of 32 g/g
Extractables of 3.1 wt. %
Residual monomers of 300 ppm
Moisture content of 2.9 wt. %
FSR of 0.59 g/gs
PSD of 200 to 600 μm
Anticaking of 3
The fluid-absorbent polymer particles were remoisturized to a moisture content of 13% by weight.
Dimension of the fluid-absorbent core: length: 37.5 cm; width: 10.0 cm.

An air through bonded acquisition-distribution layer between (A) and (C) having a basis weight of 50 gsm is rectangular shaped with dimensions of 20 cm×10 cm and smaller than the fluid-absorbent core.

The fluid-absorbent article further comprises:
flat rubber elastics; elastics from spandex type fibers: 3 leg elastics and 1 cuff elastics
leg cuffs from synthetic fibers showing the layer combination SMS and having a basis weight of between 13 to 17 gsm and a height of 4.6 cm
mechanical closure system with landing zone of dimension 18.3 cm×4.0 cm and flexiband closure tapes of 3.4 cm×1.0 cm; attached to hook fastening tape of 3.4 cm×1.4 cm
Also incorporated is elasticated waistband located to the rear of the product with dimensions of 14.6 cm×4.5 cm
Dimension of the fluid-absorbent article: length: 49.6 cm; front width: 34.0 cm; crotch width: 24.0 cm; rear width: 34.3 cm.

Embodiment 2

A further preferred embodiment of the present invention is described in Embodiment 2 hereinafter. Thus, a preferred fluid-absorbent article comprising
(A) an upper liquid-pervious layer comprising a thermalbond layer (three piece coverstock);
(B) a lower liquid-impervious layer comprising a composite of breathable polyethylene film and spunbond non-woven;
(C) a single fluid-absorbent core between (A) and (B) comprising between 40 to 80% by weight fluid-absorbent polymer particles based on the total absorbent core weight and including a multi-layered fluid-storage section comprising the following sequence:
  1. a homogenous upper core fluff layer of hydrophilic fibrous matrix of wood pulp fibers (cellulose fibers) containing about 50% of the total fluff amount;
  2. a fluid-absorbent layer comprising fluid-absorbent polymer particles; suitable fluid-absorbent polymer particles for such construction having a saline flow conductivity (SFC) from about 35 to $100 \times 10^{-7}$ cm³ s/g;
  3. a homogenous lower core fluff layer of hydrophilic fibrous matrix of wood pulp fibers (cellulose fibers) containing about 50% of the total fluff amount and acting as a dusting layer; and
(D) an air-through bonded acquisition-distribution layer between (A) and (C) having a basis weight of 40 to 80 gsm; the acquisition-distribution layer is rectangular shaped and smaller than the fluid-absorbent core having a size of about 150 to about 250 cm².

The construction of the products chassis and the components contained therein is made and controlled by the discrete application of hotmelt adhesives as known to people skilled in the art. Examples would be e.g. Dispomelt 505B, Dispomelt Cool 1101, as well as other specific function adhesives manufactured by National Starch or Henkel.

Ultra-thin high-loaded fluid-absorbent layers can be formed by immobilization of fluid-absorbent polymer particles on a non-woven sheet using hotmelt adhesives. Preferably the fluid-absorbent polymer particles form longitudinal strips or discrete spots. Other patterns of the fluid-absorbent polymer particles are also possible.

In a preferred embodiment the ultra-thin high-loaded fluid-absorbent layers comprise at least two sheets comprising immobilized fluid-absorbent polymer particles.

Examples of ultra-thin high-loaded fluid-absorbent layers are described in EP 1 293 187 A1, U.S. Pat. No. 6,972,011, EP 1 447 066 A1, EP 1 447 067 A1, EP 1 609 448 A1, JP 2004/313580, US 2005/0137085, US 2006/0004336, US 2007/0135785 WO 2008/155699 A1, WO 2008/155701 A2, WO 2008/155702 A1, WO 2008/155710 A1, WO 2008/155711 A1, WO 2004/071363 A1, US 2003/0181115, WO 2005/097025, US 2007/156108, US 2008/0125735, and WO 2008/155722 A2, which explicitly forms part of the present disclosure.

Construction Example of Embodiment 2

The fluid-absorbent core consists of a multi-layered single core system each layer having a uniform rectangular size. The layered fluid-absorbent core between (A) and (B) comprises a multi-layered system of hydrophilic fibers (cellulose fibers, fluff pulp fibers). The total fluff pulp weight is 12 g divided equally between upper core (1) and lower core (3). The density of the fluid-absorbent core is for the front overall average 0.19 g/cm$^3$, for the insult zone 0.20 g/cm$^3$, for the back overall average 0.18 g/cm$^3$. The basis weight of the fluid-absorbent core is for the front overall average 989 gsm, for the insult zone 1101 gsm, for the back overall average 664 gsm. The thickness of the fluid-absorbent core has an average of 4.5 mm.

The fluid-absorbent layer (2) holds 56.5% by weight distributed fluid-absorbent polymer particles, the quantity of fluid-absorbent polymer particles within the fluid-absorbent core is 12 g.

The fluid-absorbent polymer particles derived from dropletization polymerization as described in WO 2008/009580 A1, table 1, example 5, exhibiting the following features and absorption profile:
CRC of 28.7 g/g
SFC of 51×10$^{-7}$ cm$^3$ s/g
AUHL of 24.5 g/g
AUL of 30.3 g/g
Extractables of 2.6 wt. %
Residual monomers of 250 ppm
Moisture content of 1.6 wt. %
FSR of 0.51 g/gs
PSD of 200 to 600 µm
Anticaking of 3

The fluid-absorbent polymer particles were remoisturized to a moisture content of 13% by weight.

Dimension of the fluid-absorbent core: length: 38 cm; width: 10 cm.

An air through bonded acquisition-distribution layer between (A) and (C) having a basis weight of 50 gsm is rectangular shaped with dimensions of 24 cm×8 cm and smaller than the fluid-absorbent core.

The fluid-absorbent article further comprises:
flat rubber elastics; elastics from spandex type fibers: 3 leg elastics and 1 cuff elastics
leg cuffs from synthetic fibers showing the layer combination SMS and having a basis weight of between 13 to 17 gsm and a height of 4.6 cm
mechanical closure system with landing zone of dimension 18.3 cm×4.0 cm and flexiband closure tapes of 3.4 cm×1.0 cm; attached to hook fastening tape of 3.4 cm×1.4 cm
Also incorporated is elasticated waistband located to the rear of the product with dimensions of 14.6×4.5 cm Dimension of the fluid-absorbent article: length: 49.6 cm; front width: 34.0 cm; crotch width: 24.0 cm; rear width: 34.3 cm.

Embodiment 3

A further preferred embodiment of the present invention is described in Embodiment 3 hereinafter. Thus, a preferred fluid-absorbent article comprising
(A) an upper liquid-pervious layer comprising a spunbond web (three piece coverstock);
(B) a lower liquid-impervious layer comprising a composite of breathable polyethylene film and spunbond nonwoven;
(C) a single fluid-absorbent core between (A) and (B) comprising a mixture of wood pulp fibers (cellulose fibers) and between 10 to 50% by weight homogeneously distributed fluid-absorbent polymer particles within the fluid-absorbent core (C); suitable fluid-absorbent polymer particles for such construction having a centrifuge retention capacity (CRC) from about 32 to 60 g/g; the fluid-absorbent core is further comprising a dusting layer adjacent to the liquid-impervious layer (B) and underlying the fluid-absorbent core above; the dusting layer is a fibrous layer comprising fluff only (cellulose fibers); and
(D) an air-through bonded acquisition-distribution layer between (A) and (C) having a basis weight of 30 to 80 gsm; the acquisition-distribution layer is rectangular shaped and smaller than the fluid-absorbent core having a size of about 150 to about 250 cm$^2$.

The construction of the products chassis and the components contained therein is made and controlled by the discrete application of hotmelt adhesives as known to people skilled in the art. Examples would be e.g. Dispomelt 505B, Dispomelt Cool 1101, as well as other specific function adhesives manufactured by National Starch or Henkel.

Ultra-thin high-loaded fluid-absorbent layers can be formed by immobilization of fluid-absorbent polymer particles on a non-woven sheet using hotmelt adhesives. Preferably the fluid-absorbent polymer particles form longitudinal strips or discrete spots. Other patterns of the fluid-absorbent polymer particles are also possible.

In a preferred embodiment the ultra-thin high-loaded fluid-absorbent layers comprise at least two sheets comprising immobilized fluid-absorbent polymer particles.

Examples of ultra-thin high-loaded fluid-absorbent layers are described in EP 1 293 187 A1, U.S. Pat. No. 6,972,011, EP 1 447 066 A1, EP 1 447 067 A1, EP 1 609 448 A1, JP 2004/313580, US 2005/0137085, US 2006/0004336, US 2007/0135785 WO 2008/155699 A1, WO 2008/155701 A2, WO 2008/155702 A1, WO 2008/155710 A1, WO 2008/155711 A1, WO 2004/071363 A1, US 2003/0181115, WO 2005/097025, US 2007/156108, US 2008/0125735, and WO 2008/155722 A2, which explicitly forms part of the present disclosure.

Construction Example of Embodiment 3

The fluid-absorbent core consists of a single fluid-absorbent Core between (A) and (B) comprising a mixture of wood pulp fibers (cellulose fibers) and 37.11% by weight homogeneously distributed fluid-absorbent polymer particles within the fluid-absorbent core (C) having a uniform rectangular size. The quantity of fluid-absorbent polymer particles within the fluid-absorbent core is 11.38 g. The total fluff pulp weight is 19.25 g. The density of the fluid-absorbent core is for the front overall average 0.22 g/cm$^3$, for the insult zone 0.18 g/cm$^3$, for the back overall average 0.18 g/cm$^3$. The basis weight of the fluid-absorbent core is for the front overall average 914.18 gsm, for the insult zone 925.47 gsm, for the back overall average 886.32 gsm.

The fluid-absorbent polymer particles derived from dropletization polymerization as described in WO 2008/009580 A1, table 1, example 3, exhibiting the following features and absorption profile:
CRC of 34.8 g/g
SFC of 16×10$^{-7}$ cm$^3$ s/g
AUHL of 27.2 g/g
AUL of 32.3 g/g
Extractables of 3.0 wt. %
Residual monomers of 320 ppm
Moisture content of 1.1 wt. %
FSR of 0.58 g/gs
PSD of 200 to 600 μm
Anticaking of 3

The fluid-absorbent polymer particles were remoisturized to a moisture content of 13% by weight.

Dimension of the fluid-absorbent core: length: 39.2 cm; width: 10.0 cm.

The thickness of the fluid-absorbent core has an average of 4.7 mm.

An air through bonded acquisition-distribution layer between (A) and (C) having a basis weight of 40 gsm is rectangular shaped with dimensions of 24.4 cm×8.6 cm and smaller than the fluid-absorbent core.

The fluid-absorbent article further comprises:
- flat rubber elastics; elastics from spandex type fibers: 3 leg elastics and 1 cuff elastics
- leg cuffs from synthetic fibers showing the layer combination SMS and having a basis weight of between 13 to 17 gsm and a height of 3.0 cm
- mechanical closure system with landing zone of dimension 18.9 cm×3.8 cm and flexiband closure tapes of 1.6 cm×3.4 cm; attached to hook fastening tape of 1.3 cm×3.4 cm
- also incorporated is elasticated waistband located to the rear of the product with dimensions of 10.8 cm×2.8 cm Dimension of the fluid-absorbent article: length: 47.8 cm; front width: 31.5 cm; crotch width: 20.6 cm; rear width: 31.1 cm.

Embodiment 4

A further preferred embodiment of the present invention is described in Embodiment 4 hereinafter. Thus, a preferred fluid-absorbent article comprising (A) an upper liquid-pervious layer comprising a spunbond web (three piece coverstock);
(B) a lower liquid-impervious layer comprising a composite of breathable polyethylene film and spunbond nonwoven;
(C) a single fluid-absorbent core between (A) and (B) comprising a mixture of wood pulp fibers (cellulose fibers) and between 40 to 80% by weight homogeneously distributed fluid-absorbent polymer particles within the fluid-absorbent core; suitable fluid-absorbent polymer particles for such construction having a saline flow conductivity (SFC) from about 35 to 100×10$^{-7}$ cm$^3$ s/g; and
(D) a system of two acquisition-distribution layers between (A) and (C), comprising an upper resin bonded layer having a basis weight of 40 to 80 gsm; the upper acquisition-distribution layer is rectangular shaped having a size of about 150 to about 250 cm$^2$; the lower acquisition-distribution layer comprising of modified cellulosic fibers (e.g. from Buckeye Technologies Inc.) having a basis weight of 40 to 80 gsm and a size of about 100 to about 300 cm$^2$; both acquisition-distribution layers are smaller than the fluid-absorbent core.

The construction of the products chassis and the components contained therein is made and controlled by the discrete application of hotmelt adhesives as known to people skilled in the art. Examples would be e.g. Dispomelt 505B, Dispomelt Cool 1101, as well as other specific function adhesives manufactured by National Starch or Henkel.

Ultra-thin high-loaded fluid-absorbent layers can be formed by immobilization of fluid-absorbent polymer particles on a non-woven sheet using hotmelt adhesives. Preferably the fluid-absorbent polymer particles form longitudinal strips or discrete spots. Other patterns of the fluid-absorbent polymer particles are also possible.

In a preferred embodiment the ultra-thin high-loaded fluid-absorbent layers comprise at least two sheets comprising immobilized fluid-absorbent polymer particles.

Examples of ultra-thin high-loaded fluid-absorbent layers are described in EP 1 293 187 A1, U.S. Pat. No. 6,972,011, EP 1 447 066 A1, EP 1 447 067 A1, EP 1 609 448 A1, JP 2004/313580, US 2005/0137085, US 2006/0004336, US 2007/0135785 WO 2008/155699 A1, WO 2008/155701 A2, WO 2008/155702 A1, WO 2008/155710 A1, WO 2008/155711 A1, WO 2004/071363 A1, US 2003/0181115, WO 2005/097025, US 2007/156108, US 2008/0125735, and WO 2008/155722 A2, which explicitly forms part of the present disclosure.

Construction Example of Embodiment 4

The fluid-absorbent core consists of a single fluid-absorbent core between (A) and (B) comprising a mixture of wood pulp fibers (cellulose fibers) and 67.12% by weight homogeneously distributed fluid-absorbent polymer particles within the fluid-absorbent core (C) having a uniform rectangular size. The fluid-absorbent core is encapsulated by wrapping with a spunbond material having a basis weight of 10 gsm. The quantity of fluid-absorbent polymer particles within the fluid-absorbent core is 12.18 g. The total fluff pulp weight is 5.95 g. The density of the fluid-absorbent core is for the front overall average 0.19 g/cm$^3$, for the insult zone 0.18 g/cm$^3$, for the back overall average 0.18 g/cm$^3$. The basis weight of the fluid-absorbent core is for the front overall average 965.79 gsm, for the insult zone 913.38 gsm, for the back overall average 658.85 gsm.

The fluid-absorbent polymer particles derived from dropletization polymerization as described in WO 2008/009598 A1, example 7, exhibiting the following features and absorption profile:
CRC of 20.9 g/g
SFC of 149×10$^{-7}$ cm$^3$ s/g
AUHL of 18.8 g/g
AUL of 22.3 g/g
Extractables of 1.6 wt. %
Residual monomers of 330 ppm
Moisture content of 16.6 wt. %
FSR of 0.28 g/gs
PSD of 200 to 600 μm
Anticaking of 3

Dimension of the fluid-absorbent core: length: 40.0 cm; width: 10.0 cm.

The thickness of the fluid-absorbent core has an average of 4.4 mm.

An air through bonded acquisition-distribution layer between (A) and (C) having a basis weight of 60 gsm is rectangular shaped with dimensions of 24.0 cm×7.5 cm and smaller than the fluid-absorbent core.

The fluid-absorbent article further comprises:
- flat rubber elastics; elastics from spandex type fibers: 3 leg elastics and 2 cuff elastics
- leg cuffs from synthetic fibers showing the layer combination SMS and having a basis weight of between 13 to 17 gsm and a height of 3.3 cm
- mechanical closure system with landing zone of dimension 19.8 cm×5.0 cm and flexiband closure tapes of 3.5 cm×2.7 cm consisting of pressure sensitive adhesive zone 3.5 cm×1.5 cm and mechanical hook of 3.5 cm×1.2 cm For improving the fit of the fluid-absorbent article, the product of embodiment 4 provides a stretchable side panel and a reduced width chassis.

Dimension of the fluid-absorbent article: length: 48.0 cm; front width: 32.3 cm; crotch width: 20.3 cm; rear width: 31.0 cm.

Embodiment 5

A further preferred embodiment of the present invention is described in Embodiment 5 hereinafter. Thus, a preferred fluid-absorbent article comprising
(A) an upper liquid-pervious layer comprising a spunbond layer (three piece coverstock);
(B) a lower liquid-impervious layer comprising a composite of breathable polyethylene film and spunbond nonwoven;
(C) a double fluid-absorbent core between (A) and (B) comprising a homogenous mixture of wood pulp fibers (cellulose fibers) and fluid-absorbent polymer particles as primary core and a layered secondary fluid-absorbent core; the total double fluid-absorbent core comprising the following sequence:
1. a homogenous primary core of hydrophilic fibrous matrix of wood pulp fibers (cellulose fibers) comprising between 10 to 50% by weight fluid-absorbent polymer particles based on the primary absorbent core weight; the primary core contains about 30% of the total fluff amount; suitable fluid-absorbent polymer particles for such construction having a centrifuge retention capacity (CRC) from about 32 to 60 g/g;
2. a secondary core upper fluff layer of hydrophilic fibrous matrix of wood pulp fibers (cellulose fibers); the secondary core upper layer contains about 35% of the total fluff amount;
3. a fluid-absorbent layer comprising between 10 to 50% by weight fluid-absorbent polymer particles based on the secondary absorbent core weight; suitable fluid-absorbent polymer particles for such construction having a centrifuge retention capacity CRC from about 32 to 60 g/g;
4. a secondary core lower fluff layer of hydrophilic fibrous matrix of wood pulp fibers (cellulose fibers) acting as a dusting layer; the lower core contains about 35% of the total fluff amount; and
(D) an air through bonded acquisition-distribution layer between (A) and (C) having a basis weight of 30 to 80 gsm; the acquisition-distribution layer is rectangular shaped and smaller than the primary fluid-absorbent core having a size of about 150 to about 250 cm².

The construction of the products chassis and the components contained therein is made and controlled by the discrete application of hotmelt adhesives as known to people skilled in the art. Examples would be e.g. Dispomelt 505B, Dispomelt Cool 1101, as well as other specific function adhesives manufactured by National Starch or Henkel.

Ultra-thin high-loaded fluid-absorbent layers can be formed by immobilization of fluid-absorbent polymer particles on a non-woven sheet using hotmelt adhesives. Preferably the fluid-absorbent polymer particles form longitudinal strips or discrete spots. Other patterns of the fluid-absorbent polymer particles are also possible.

In a preferred embodiment the ultra-thin high-loaded fluid-absorbent layers comprise at least two sheets comprising immobilized fluid-absorbent polymer particles.

Examples of ultra-thin high-loaded fluid-absorbent layers are described in EP 1 293 187 A1, U.S. Pat. No. 6,972,011, EP 1 447 066 A1, EP 1 447 067 A1, EP 1 609 448 A1, JP 2004/313580, US 2005/0137085, US 2006/0004336, US 2007/0135785 WO 2008/155699 A1, WO 2008/155701 A2, WO 2008/155702 A1, WO 2008/155710 A1, WO 2008/155711 A1, WO 2004/071363 A1, US 2003/0181115, WO 2005/097025, US 2007/156108, US 2008/0125735, and WO 2008/155722 A2, which explicitly forms part of the present disclosure.

Construction Example of Embodiment 5

The total fluid-absorbent core includes a double-core system, the primary and secondary cores each having an almost uniform rectangular size. The primary core is smaller than the secondary core and is positioned 6 cm from the front distal edge of the secondary core and 10 cm from the rear distal edge of the secondary core and is 9 cm in width. The primary fluid-absorbent core between (A) and (B) comprising a homogenous mixture of hydrophilic fibrous matrix of wood pulp fibers and 25% by weight of water absorbent polymer particles. The primary core has a total weight of 8 g. The secondary core is a multi-layered system of hydrophilic fibrous matrix of wood pulp fibers (cellulose fibers) and 30% by weight fluid-absorbent polymer particles. The quantity of fluid-absorbent polymer particles within the secondary fluid-absorbent core is 6.0 g. The density of the fluid-absorbent core is for the front overall average 0.15 g/cm³, for the insult zone 0.19 g/cm³, for the back overall average 0.18 g/cm³. The basis weight of the fluid-absorbent core is for the front overall average 790.63 gsm, for the insult zone 1121.38 gsm, for the back overall average 976.83 gsm.

The fluid-absorbent polymer particles derived from dropletization polymerization as described in WO 2008/009580 A1, table 2, example 3, exhibiting the following features and absorption profile:
CRC of 35.7 g/g
SFC of $10 \times 10^{-7}$ cm³ s/g
AUHL of 29.1 g/g
AUL of 35.0 g/g
Extractables of 3.0 wt. %
Residual monomers of 250 ppm
Moisture content of 0.9 wt. %
FSR of 0.59 g/gs
PSD of 200 to 600 μm
Anticaking of 3

The fluid-absorbent polymer particles were remoisturized to a moisture content of 13% by weight.

Dimension of the secondary fluid-absorbent core: length: 40.8 cm; front width: 10.5 cm; crotch width: 9.3 cm; rear width: 10.3 cm.

The total thickness of both fluid-absorbent cores has an average of 5.4 mm.

An air through bonded acquisition-distribution layer between (A) and (C) having a basis weight of 40 gsm is rectangular shaped and smaller than the primary fluid-absorbent core having a size of 19.7 cm×7.6 cm.

The fluid-absorbent article further comprises:
flat rubber elastics; elastics from spandex type fibers: 3 leg elastics and 2 cuff elastics
leg cuffs from synthetic fibers showing the layer combination SMS and having a basis weight of between 13 to 17 gsm and a height of 3.8 cm
mechanical closure system with landing zone of dimension 22.0 cm×4.0 cm and flexiband closure tapes of 3.4 cm×1.5 cm; attached to hook fastening tape of 3.4 cm×1.4 cm
Dimension of the fluid-absorbent article: length: 48.0 cm; front width: 29.7 cm; crotch width: 22.0 cm; rear width: 31.6 cm.

Embodiment 6

A further preferred embodiment of the present invention is described in Embodiment 6 hereinafter. Thus, a preferred fluid-absorbent article comprising
  (A) an upper liquid-pervious layer comprising a spunbond layer (three piece coverstock);
  (B) a lower liquid-impervious layer comprising a composite of breathable polyethylene film and spunbond nonwoven;
  (C) a double fluid-absorbent core between (A) and (B) comprising a homogenous mixture of wood pulp fibers (cellulose fibers) and fluid-absorbent polymer particles as primary core and a layered secondary fluid-absorbent core; the total double fluid-absorbent core comprising the following sequence:
    1. a homogenous primary core of hydrophilic fibrous matrix of wood pulp fibers (cellulose fibers) comprising between 40 to 80% by weight fluid-absorbent polymer particles based on the primary absorbent core weight; the primary core contains about 50% of the total fluff amount; suitable fluid-absorbent polymer particles for such construction having a saline flow conductivity (SFC) from about 35 to $100 \times 10^{-7}$ cm$^3$ s/g;
    2. a secondary core upper fluff layer of hydrophilic fibrous matrix of wood pulp fibers (cellulose fibers); the secondary core upper layer contains about 25% of the total fluff amount;
    3. a fluid-absorbent layer comprising between 40 to 80% by weight fluid-absorbent polymer particles based on the secondary absorbent core weight; suitable fluid-absorbent polymer particles for such construction having a saline flow conductivity (SFC) from about 35 to $100 \times 10^{-7}$ cm$^3$ s/g;
    4. a secondary core lower fluff layer of hydrophilic fibrous matrix of wood pulp fibers (cellulose fibers) acting as a dusting layer; the lower core contains about 25% of the total fluff amount; and
  (D) an air through bonded acquisition-distribution layer between (A) and (C) having a basis weight of 40 to 80 gsm; the acquisition-distribution layer is rectangular shaped and smaller than the primary fluid-absorbent core having a size of about 150 to about 250 cm$^2$.

The construction of the products chassis and the components contained therein is made and controlled by the discrete application of hotmelt adhesives as known to people skilled in the art. Examples would be e.g. Dispomelt 505B, Dispomelt Cool 1101, as well as other specific function adhesives manufactured by National Starch or Henkel.

Ultra-thin high-loaded fluid-absorbent layers can be formed by immobilization of fluid-absorbent polymer particles on a non-woven sheet using hotmelt adhesives. Preferably the fluid-absorbent polymer particles form longitudinal strips or discrete spots. Other patterns of the fluid-absorbent polymer particles are also possible.

In a preferred embodiment the ultra-thin high-loaded fluid-absorbent layers comprise at least two sheets comprising immobilized fluid-absorbent polymer particles.

Examples of ultra-thin high-loaded fluid-absorbent layers are described in EP 1 293 187 A1, U.S. Pat. No. 6,972,011, EP 1 447 066 A1, EP 1 447 067 A1, EP 1 609 448 A1, JP 2004/313580, US 2005/0137085, US 2006/0004336, US 2007/0135785 WO 2008/155699 A1, WO 2008/155701 A2, WO 2008/155702 A1, WO 2008/155710 A1, WO 2008/155711 A1, WO 2004/071363 A1, US 2003/0181115, WO 2005/097025, US 2007/156108, US 2008/0125735, and WO 2008/155722 A2, which explicitly forms part of the present disclosure.

Construction Example of Embodiment 6

The total fluid-absorbent core includes a double-core system, the primary and secondary cores each having an almost uniform rectangular size. The primary core is smaller than the secondary core and is positioned 6 cm from the front distal edge of the secondary core and 10 cm from the rear distal edge of the secondary core and is 9 cm in width. The primary fluid-absorbent core between (A) and (B) comprising a homogenous mixture of hydrophilic fibrous matrix of wood pulp fibers and 50% by weight of water absorbent polymer particles. The primary core has a total weight of 8 g. The secondary core is a multi-layered system of hydrophilic fibrous matrix of wood pulp fibers (cellulose fibers) and 50% by weight fluid-absorbent polymer particles. The quantity of fluid-absorbent polymer particles within the secondary fluid-absorbent core is 10.0 g. The density of the fluid-absorbent core is for the front overall average 0.19 g/cm$^3$, for the insult zone 0.19 g/cm$^3$, for the back overall average 0.18 g/cm$^3$. The basis weight of the fluid-absorbent core is for the front overall average 813.46 gsm, for the insult zone 1209.15 gsm, for the back overall average 986.27 gsm.

The fluid-absorbent polymer particles derived from dropletization polymerization as described in WO 2008/009580 A1, table 2, example 6, exhibiting the following features and absorption profile:
CRC of 27.7 g/g
SFC of $65 \times 10^{-7}$ cm$^3$ s/g
AUHL of 23.4 g/g
AUL of 28.9 g/g
Extractables of 3.3 wt. %
Residual monomers of 280 ppm
Moisture content of 1.2 wt. %
FSR of 0.34 g/gs
PSD of 200 to 600 µm
Anticaking of 3

The fluid-absorbent polymer particles were remoisturized to a moisture content of 13% by weight.

Dimension of the secondary fluid-absorbent core: length: 40.8 cm; front width: 10.0 cm; crotch width: 9.0 cm; rear width: 10.0 cm.

The total thickness of both fluid-absorbent cores has an average of 3.9 mm.

An air through bonded acquisition-distribution layer between (A) and (C) having a basis weight of 60 gsm is rectangular shaped and smaller than the primary fluid-absorbent core having a size of 19.0 cm×7.6 cm.

The fluid-absorbent article further comprises:
- flat rubber elastics; elastics from spandex type fibers: 3 leg elastics and 2 cuff elastics
- leg cuffs from synthetic fibers showing the layer combination SMS and having a basis weight of between 13 to 17 gsm and a height of 3.8 cm
- mechanical closure system with landing zone of dimension 22.0 cm×4.0 cm and flexiband closure tapes of 3.4 cm×1.5 cm; attached to hook fastening tape of 3.4 cm×1.4 cm Dimension of the fluid-absorbent article: length: 48.0 cm; front width: 29.7 cm; crotch width: 20.0 cm; rear width: 31.6 cm.

Embodiment 7

A further preferred embodiment of the present invention is described in Embodiment 7 hereinafter. Thus, a preferred fluid-absorbent article comprising
- (A) an upper liquid-pervious layer comprising a spunbond layer (three piece coverstock);
- (B) a lower liquid-impervious layer comprising a composite of breathable polyethylene film and spunbond nonwoven;
- (C) a double fluid-absorbent core between (A) and (B) comprising a homogenous mixture of wood pulp fibers (cellulose fibers) and polymer particles for each the primary core and the secondary fluid-absorbent core; the total double fluid-absorbent core comprising:
  1. a homogenous primary core of hydrophilic fibrous matrix of wood pulp fibers (cellulose fibers) comprising between 10 to 50% by weight fluid-absorbent polymer particles based on the primary absorbent core weight; the primary core contains about 30% of the total fluff amount; suitable fluid-absorbent polymer particles for such construction having a centrifuge retention capacity (CRC) from about 32 to 60 g/g;
  2. a homogenous secondary core of hydrophilic fibrous matrix of wood pulp fibers (cellulose fibers) comprising between 10 to 50% by weight fluid-absorbent polymer particles based on the secondary absorbent core weight; the secondary core contains about 70% of the total fluff amount; suitable fluid-absorbent polymer particles for such construction having a centrifuge retention capacity (CRC) from about 32 to 60 g/g; and
- (D) an air through bonded acquisition-distribution layer between (A) and (C) having a basis weight of 30 to 80 gsm; the acquisition-distribution layer is rectangular shaped and smaller than the primary fluid-absorbent core having a size of about 150 to about 250 cm².

The construction of the products chassis and the components contained therein is made and controlled by the discrete application of hotmelt adhesives as known to people skilled in the art. Examples would be e.g. Dispomelt 505B, Dispomelt Cool 1101, as well as other specific function adhesives manufactured by National Starch or Henkel.

Ultra-thin high-loaded fluid-absorbent layers can be formed by immobilization of fluid-absorbent polymer particles on a non-woven sheet using hotmelt adhesives. Preferably the fluid-absorbent polymer particles form longitudinal strips or discrete spots. Other patterns of the fluid-absorbent polymer particles are also possible.

In a preferred embodiment the ultra-thin high-loaded fluid-absorbent layers comprise at least two sheets comprising immobilized fluid-absorbent polymer particles.

Examples of ultra-thin high-loaded fluid-absorbent layers are described in EP 1 293 187 A1, U.S. Pat. No. 6,972,011, EP 1 447 066 A1, EP 1 447 067 A1, EP 1 609 448 A1, JP 2004/313580, US 2005/0137085, US 2006/0004336, US 2007/0135785 WO 2008/155699 A1, WO 2008/155701 A2, WO 2008/155702 A1, WO 2008/155710 A1, WO 2008/155711 A1, WO 2004/071363 A1, US 2003/0181115, WO 2005/097025, US 2007/156108, US 2008/0125735, and WO 2008/155722 A2, which explicitly forms part of the present disclosure.

Construction Example of Embodiment 7

The total fluid-absorbent core includes a double-core system, the primary and secondary cores each having an almost uniform rectangular size. The primary core is smaller than the secondary core and is positioned 6 cm from the front distal edge of the secondary core and 10 cm from the rear distal edge of the secondary core and is 9 cm in width. The primary fluid-absorbent core between (A) and the secondary fluid-absorbent core comprising a homogenous mixture of hydrophilic fibrous matrix of wood pulp fibers and 25% by weight of water absorbent polymer particles. The primary core has a total weight of 8 g. The secondary core between the primary core and (B) comprising a homogenous mixture of hydrophilic fibrous matrix of wood pulp fibers and 30% by weight of water absorbent polymer particles. The quantity of fluid-absorbent polymer particles within the secondary fluid-absorbent core is 6.0 g. The secondary core has a total weight of 20 g. The density of the fluid-absorbent core is for the front overall average 0.15 g/cm³, for the insult zone 0.19 g/cm³, for the back overall average 0.18 g/cm³. The basis weight of the fluid-absorbent core is for the front overall average 790.63 gsm, for the insult zone 1121.38 gsm, for the back overall average 976.83 gsm.

The fluid-absorbent polymer particles derived from dropletization polymerization as described in WO 2008/009580 A1, table 2, example 3, exhibiting the following features and absorption profile:
CRC of 35.7 g/g
SFC of $10 \times 10^{-7}$ cm³ s/g
AUHL of 29.1 g/g
AUL of 35.0 g/g
Extractables of 3.0 wt. %
Residual monomers of 250 ppm
Moisture content of 0.9 wt. %
FSR of 0.59 g/gs
PSD of 200 to 600 μm
Anticaking of 3

The fluid-absorbent polymer particles were remoisturized to a moisture content of 13% by weight.

Dimension of the secondary fluid-absorbent core: length: 40.8 cm; front width: 10.5 cm; crotch width: 9.3 cm; rear width: 10.3 cm The total thickness of both fluid-absorbent cores has an average of 5.4 mm.

An air through bonded acquisition-distribution layer between (A) and (C) having a basis weight of 40 gsm is rectangular shaped and smaller than the primary fluid-absorbent core having a size of 19/cm×7.6 cm.

The fluid-absorbent article further comprises:
- flat rubber elastics; elastics from spandex type fibers: 3 leg elastics and 2 cuff elastics
- leg cuffs from synthetic fibers showing the layer combination SMS and having a basis weight of between 13 to 17 gsm and a height of 3.8 cm
- mechanical closure system with landing zone of dimension 22.0 cm×4.0 cm and flexiband closure tapes of 3.4 cm×1.5 cm; attached to hook fastening tape of 3.4 cm×1.4 cm Dimension of the fluid-absorbent article: length: 48.0 cm; front width: 29.7 cm; crotch width: 22.0 cm; rear width: 31.6 cm.

Embodiment 8

A further preferred embodiment of the present invention is described in Embodiment 8 hereinafter. Thus, a preferred fluid-absorbent article comprising
- (A) an upper liquid-pervious layer comprising a spunbond layer (three piece coverstock);
- (B) a lower liquid-impervious layer comprising a composite of breathable polyethylene film and spunbond non-woven;
- (C) a double fluid-absorbent core between (A) and (B) comprising a homogenous mixture of wood pulp fibers (cellulose fibers) and polymer particles for each the primary core and the secondary fluid-absorbent core; the total double fluid-absorbent core comprising:
  1. a homogenous primary core of hydrophilic fibrous matrix of wood pulp fibers (cellulose fibers) comprising between 40 to 80% by weight fluid-absorbent polymer particles based on the primary absorbent core weight; the primary core contains about 50% of the total fluff amount; suitable fluid-absorbent polymer particles for such construction having a saline flow conductivity (SFC) from about 35 to $100 \times 10^{-7}$ cm$^3$ s/g;
  2. a homogenous secondary core of hydrophilic fibrous matrix of wood pulp fibers (cellulose fibers) comprising between 40 to 70% by weight fluid-absorbent polymer particles based on the secondary absorbent core weight; the secondary core contains about 50% of the total fluff amount; suitable fluid-absorbent polymer particles for such construction having a saline flow conductivity (SFC) from about 35 to $100 \times 10^{-7}$ cm$^3$ s/g; and
- (D) an air through bonded acquisition-distribution layer between (A) and (C) having a basis weight of 40 to 80 gsm; the acquisition-distribution layer is rectangular shaped and smaller than the primary fluid-absorbent core having a size of about 150 to about 250 cm$^2$.

The construction of the products chassis and the components contained therein is made and controlled by the discrete application of hotmelt adhesives as known to people skilled in the art. Examples would be e.g. Dispomelt 505B, Dispomelt Cool 1101, as well as other specific function adhesives manufactured by National Starch or Henkel.

Ultra-thin high-loaded fluid-absorbent layers can be formed by immobilization of fluid-absorbent polymer particles on a non-woven sheet using hotmelt adhesives. Preferably the fluid-absorbent polymer particles form longitudinal strips or discrete spots. Other patterns of the fluid-absorbent polymer particles are also possible.

In a preferred embodiment the ultra-thin high-loaded fluid-absorbent layers comprise at least two sheets comprising immobilized fluid-absorbent polymer particles.

Examples of ultra-thin high-loaded fluid-absorbent layers are described in EP 1 293 187 A1, U.S. Pat. No. 6,972,011, EP 1 447 066 A1, EP 1 447 067 A1, EP 1 609 448 A1, JP 2004/313580, US 2005/0137085, US 2006/0004336, US 2007/0135785 WO 2008/155699 A1, WO 2008/155701 A2, WO 2008/155702 A1, WO 2008/155710 A1, WO 2008/155711 A1, WO 2004/071363 A1, US 2003/0181115, WO 2005/097025, US 2007/156108, US 2008/0125735, and WO 2008/155722 A2, which explicitly forms part of the present disclosure.

Construction Example of Embodiment 8

The total fluid-absorbent core includes a double-core system, the primary and secondary cores each having an almost uniform rectangular size. The primary core is smaller than the secondary core and is positioned 6 cm from the front distal edge of the secondary core and 10 cm from the rear distal edge of the secondary core and is 9 cm in width. The primary fluid-absorbent core between (A) and the secondary fluid-absorbent core comprising a homogenous mixture of hydrophilic fibrous matrix of wood pulp fibers and 28.6% by weight of water absorbent polymer particles. The primary core has a total weight of 8 g. The secondary core between the primary core and (B) comprising a homogenous mixture of hydrophilic fibrous matrix of wood pulp fibers and 71.4% by weight of water absorbent polymer particles. The quantity of fluid-absorbent polymer particles within the secondary fluid-absorbent core is 10.0 g. The secondary core has a total weight of 20 g. The density of the fluid-absorbent core is for the front overall average 0.15 g/cm$^3$, for the insult zone 0.19 g/cm$^3$, for the back overall average 0.18 g/cm$^3$. The basis weight of the fluid-absorbent core is for the front overall average 790.63 gsm, for the insult zone 1121.38 gsm, for the back overall average 976.83 gsm.

The fluid-absorbent polymer particles derived from dropletization polymerization as described in WO 2008/009580 A1, table 2, example 6, exhibiting the following features and absorption profile:
CRC of 27.7 g/g
SFC of $65 \times 10^{-7}$ cm$^3$ s/g
AUHL of 23.4 g/g
AUL of 28.9 g/g
Extractables of 3.3 wt. %
Residual monomers of 280 ppm
Moisture content of 1.2 wt. %
FSR of 0.34 g/gs
PSD of 200 to 600 μm
Anticaking of 3

The fluid-absorbent polymer particles were remoisturized to a moisture content of 13% by weight.

Dimension of the secondary fluid-absorbent core: length: 40.8 cm; front width: 10.5 cm; crotch width: 9.3 cm; rear width: 10.3 cm.

The total thickness of both fluid-absorbent cores has an average of 5.4 mm.

An air through bonded acquisition-distribution layer between (A) and (C) having a basis weight of 60 gsm is rectangular shaped and smaller than the primary fluid-absorbent core having a size of 19.7 cm×7.6 cm.

The fluid-absorbent article further comprises:
- flat rubber elastics; elastics from spandex type fibers: 3 leg elastics and 2 cuff elastics
- leg cuffs from synthetic fibers showing the layer combination SMS and having a basis weight of between 13 to 17 gsm and a height of 3.8 cm mechanical closure system with landing zone of dimension 22.0 cm×4.0 cm and flexiband closure tapes of 3.4 cm×1.5 cm; attached to hook fastening tape of 3.4 cm×1.4 cm Dimension of the fluid-absorbent article: length: 48.0 cm; front width: 29.7 cm; crotch width: 20.0 cm; rear width: 31.6 cm.

Embodiment 9

A further preferred embodiment of the present invention is described in Embodiment 9 (pantiliner) hereinafter. Thus, a preferred fluid-absorbent article comprising
  (A) an upper liquid-pervious layer comprising a spunbond layer (three piece coverstock);
  (B) a lower liquid-impervious layer comprising a composite of breathable polyethylene film and spunbond nonwoven;
  (C) a single fluid-absorbent core between (A) and (B) comprising between 10 to 50% by weight fluid-absorbent polymer particles based on the total absorbent core weight and including a multi-layered fluid-storage section comprising the following sequence:
    1. a homogenous upper core fluff layer of hydrophilic fibrous matrix of wood pulp fibers (cellulose fibers) containing about 50% of the total fluff amount;
    2. a fluid-absorbent layer comprising fluid-absorbent polymer particles; suitable fluid-absorbent polymer particles for such construction having a centrifuge retention capacity (CRC) from about 32 to 60 g/g; and
  (D) an air through bonded acquisition-distribution layer between (A) and (C) having a basis weight of 40 to 80 gsm; the acquisition-distribution layer is rectangular shaped and smaller than the primary fluid-absorbent core having a size of about 150 to about 250 $cm^2$.

The construction of the products chassis and the components contained therein is made and controlled by the discrete application of hotmelt adhesives as known to people skilled in the art. Examples would be e.g. Dispomelt 505B, Dispomelt Cool 1101, as well as other specific function adhesives manufactured by National Starch or Henkel.

Ultra-thin high-loaded fluid-absorbent layers can be formed by immobilization of fluid-absorbent polymer particles on a non-woven sheet using hotmelt adhesives. Preferably the fluid-absorbent polymer particles form longitudinal strips or discrete spots. Other patterns of the fluid-absorbent polymer particles are also possible.

In a preferred embodiment the ultra-thin high-loaded fluid-absorbent layers comprise at least two sheets comprising immobilized fluid-absorbent polymer particles.

Examples of ultra-thin high-loaded fluid-absorbent layers are described in EP 1 293 187 A1, U.S. Pat. No. 6,972,011, EP 1 447 066 A1, EP 1 447 067 A1, EP 1 609 448 A1, JP 2004/313580, US 2005/0137085, US 2006/0004336, US 2007/0135785 WO 2008/155699 A1, WO 20013/155701 A2, WO 2008/155702 A1, WO 2008/155710 A1, WO 2008/155711 A1, WO 2004/071363 A1, US 2003/0181115, WO 2005/097025, US 2007/156108, US 2008/0125735, and WO 2008/155722 A2, which explicitly forms part of the present disclosure.

Construction Example of Embodiment 9

The fluid-absorbent core consists of a double-layered single core system each layer having a uniform rectangular size. The layered fluid-absorbent core between (A) and (B) comprises a double-layered system of hydrophilic fibers (cellulose fibers, fluff pulp fibers), each layer having an almost uniform rectangular size. The fluid-absorbent core is encapsulated by wrapping with a spunbond material having a basis weight of 10 gsm. The density of the fluid-absorbent core is for the font overall average 0.16 $g/cm^3$, for the insult zone 0.14 $g/cm^3$, for the back overall average 0.16 $g/cm^3$. The basis weight of the fluid-absorbent core is for the front overall average 598.16 gsm, for the insult zone 596.94 gsm, for the back overall average 626.23 gsm. The thickness of the fluid-absorbent core has an average of 3.8 mm.

The fluid-absorbent core holds 31.38% by weight distributed fluid-absorbent polymer particles, the quantity of fluid-absorbent polymer particles within the fluid-absorbent core is 9.34 g.

The fluid-absorbent polymer particles derived from dropletization polymerization as described in WO 2008/009580 A1, table 1, example 2, exhibiting the following features and absorption profile:
CRC of 37.2 g/g
SFC of $10 \times 10^{-7}$ $cm^3$ s/g
AUHL of 28.1 g/g
AUL of 32 g/g
Extractables of 3.1 wt. %
Residual monomers of 300 ppm
Moisture content of 2.9 wt. %
FSR of 0.59 g/gs
PSD of 200 to 600 μm
Anticaking of 3

The fluid-absorbent polymer particles were remoisturized to a moisture content of 13% by weight.

Dimension of the fluid-absorbent core: length: 40.8 cm; front width: 14.2 cm; crotch width: 14.5 cm; rear width: 14.1 cm.

An air through bonded acquisition-distribution layer between (A) and (C) having a basis weight of 35.7 gsm is rectangular shaped and smaller than the fluid-absorbent core having a size of 24.0 cm×9.2 cm.

The fluid-absorbent article further comprises:
  flat rubber elastics; elastics from spandex type fibers: 5 cuff elastics
  leg cuffs from synthetic fibers showing the layer combination SMS and having a basis weight of between 13 to 17 gsm and a height of 4.7 cm For improving the fit of the fluid-absorbent article, the pantiliner of embodiment 10 provides stretchable bands.

Dimension of the fluid-absorbent article: length: 47.9 cm; front width: 31.3 cm; crotch width: 15.4 cm; rear width: 31.3 cm.

Embodiment 10

A further preferred embodiment of the present invention is described in Embodiment 10 (pantiliner) hereinafter. Thus, a preferred fluid-absorbent article comprising
  (A) an upper liquid-pervious layer comprising a spunbond layer (three piece coverstock);
  (B) a lower liquid-impervious layer comprising a composite of breathable polyethylene film and spunbond nonwoven;
  (C) a single fluid-absorbent core between (A) and (B) comprising between 40 to 80% by weight fluid-absorbent polymer particles based on the total absorbent core weight and including a multi-layered fluid-storage section comprising the following sequence:
    1. a homogenous upper core fluff layer of hydrophilic fibrous matrix of wood pulp fibers (cellulose fibers) containing about 50% of the total fluff amount;

2. a fluid-absorbent layer comprising fluid-absorbent polymer particles; suitable fluid-absorbent polymer particles for such construction having a saline flow conductivity (SFC) from about 35 to $100 \times 10^{-7}$ cm$^3$ s/g; and (D) an air through bonded acquisition-distribution layer between (A) and (C) having a basis weight of 40 to 80 gsm; the acquisition-distribution layer is rectangular shaped and smaller than the primary fluid-absorbent core having a size of about 150 to about 250 cm$^2$.

The construction of the products chassis and the components contained therein is made and controlled by the discrete application of hotmelt adhesives as known to people skilled in the art. Examples would be e.g. Dispomelt 505B, Dispomelt Cool 1101, as well as other specific function adhesives manufactured by National Starch or Henkel.

Ultra-thin high-loaded fluid-absorbent layers can be formed by immobilization of fluid-absorbent polymer particles on a non-woven sheet using hotmelt adhesives. Preferably the fluid-absorbent polymer particles form longitudinal strips or discrete spots. Other patterns of the fluid-absorbent polymer particles are also possible.

In a preferred embodiment the ultra-thin high-loaded fluid-absorbent layers comprise at least two sheets comprising immobilized fluid-absorbent polymer particles.

Examples of ultra-thin high-loaded fluid-absorbent layers are described in EP 1 293 187 A1, U.S. Pat. No. 6,972,011, EP 1 447 066 A1, EP 1 447 067 A1, EP 1 609 448 A1, JP 2004/313580, US 2005/0137085, US 2006/0004336, US 2007/0135785 WO 2008/155699 A1, WO 2008/155701 A2, WO 2008/155702 A1, WO 2008/155710 A1, WO 2008/155711 A1, WO 2004/071363 A1, US 2003/0181115, WO 2005/097025, US 2007/156108, US 2008/0125735, and WO 2008/155722 A2, which explicitly forms part of the present disclosure.

Construction Example of Embodiment 10

The fluid-absorbent core consists of a double-layered single core system each layer having a uniform rectangular size. The layered fluid-absorbent core between (A) and (B) comprises a double-layered system of hydrophilic fibers (cellulose fibers, fluff pulp fibers), each layer having an almost uniform rectangular size. The fluid-absorbent core is encapsulated by wrapping with a spunbond material having a basis weight of 10 gsm. The density of the fluid-absorbent core is for the font overall average 0.16 g/cm$^3$, for the insult zone 0.14 g/cm$^3$, for the back overall average 0.16 g/cm$^3$. The basis weight of the fluid-absorbent core is for the front overall average 598.16 gsm, for the insult zone 596.94 gsm, for the back overall average 626.23 gsm. The thickness of the fluid-absorbent core has an average of 3.8 mm.

The fluid-absorbent core holds 59.05% by weight distributed fluid-absorbent polymer particles, the quantity of fluid-absorbent polymer particles within the fluid-absorbent core is 11.9 g.

The fluid-absorbent polymer particles derived from dropletization polymerization as described in WO 2008/009598 A1, example 6, exhibiting the following features and absorption profile:
CRC of 24.5 g/g
SFC of $41 \times 10^{-7}$ cm$^3$ s/g
AUHL of 18.6 g/g
AUL of 24.1 g/g
Extractables of 3.8 wt. %
Residual monomers of 310 ppm
Moisture content of 15.9 wt. %
FSR 0.93 g/gs
PSD of 200 to 600 µm
Anticaking of 3
Dimension of the fluid-absorbent core: length: 40.8 cm; front width: 14.2 cm; crotch width: 14.5 cm; rear width: 14.1 cm.

An air through bonded acquisition-distribution layer between (A) and (C) having a basis weight of 35.7 gsm is rectangular shaped and smaller than the fluid-absorbent core having a size of 24.0 cm×9.2 cm.

The fluid-absorbent article further comprises:
flat rubber elastics; elastics from spandex type fibers: 5 cuff elastics
leg cuffs from synthetic fibers showing the layer combination SMS and having a basis weight of between 13 to 17 gsm and a height of 4.7 cm For improving the fit of the fluid-absorbent article, the pantiliner of embodiment 10 provides stretchable bands.

Dimension of the fluid-absorbent article: length: 47.9 cm; front width: 31.3 cm; crotch width: 15.4 cm; rear width: 31.3 cm.

Embodiment 11

A further preferred embodiment of the present invention is described in Embodiment 11 (pantiliner) hereinafter. Thus, a preferred fluid-absorbent article comprising (A) an upper liquid-pervious layer comprising a spunbond layer (three piece coverstock);
(B) a lower liquid-impervious layer comprising a composite of breathable polyethylene film and spunbond non-woven;
(C) a high-loaded single fluid-absorbent core between (A) and (B) comprising between 55 to 95% by weight fluid-absorbent polymer particles based on the total absorbent core weight and including a multi-layered fluid-storage section comprising the following sequence:
1. a homogenous upper core layer of hydrophilic synthetic fibers (fibrous matrix) containing about 95% of the total fluff amount;
2. a high-loaded fluid-absorbent layer comprising fluid-absorbent polymer particles; suitable fluid-absorbent polymer particles for such construction having a saline flow conductivity (SFC) from about 50 to $150 \times 10^{-7}$ cm$^3$ s/g; and
(D) an air through bonded acquisition-distribution layer between (A) and (C) having a basis weight of 40 to 80 gsm; the acquisition-distribution layer is rectangular shaped and smaller than the primary fluid-absorbent core having a size of about 150 to about 250 cm$^2$.

The construction of the products chassis and the components contained therein is made and controlled by the discrete application of hotmelt adhesives as known to people skilled in the art. Examples would be e.g. Dispomelt 505B, Dispomelt Cool 1101, as well as other specific function adhesives manufactured by National Starch or Henkel.

Ultra-thin high-loaded fluid-absorbent layers can be formed by immobilization of fluid-absorbent polymer particles on a non-woven sheet using hotmelt adhesives. Preferably the fluid-absorbent polymer particles form longitudinal strips or discrete spots. Other patterns of the fluid-absorbent polymer particles are also possible.

In a preferred embodiment the ultra-thin high-loaded fluid-absorbent layers comprise at least two sheets comprising immobilized fluid-absorbent polymer particles.

Examples of ultra-thin high-loaded fluid-absorbent layers are described in EP 1 293 187 A1, U.S. Pat. No. 6,972,011, EP 1 447 066 A1, EP 1 447 067 A1, EP 1 609 448 A1, JP 2004/313580, US 2005/0137085, US 2006/0004336, US 2007/0135785 WO 2008/155699 A1, WO 2008/155701 A2, WO 2008/155702 A1, WO 2008/155710 A1, WO 2008/155711 A1, WO 2004/071363 A1, US 2003/0181115, WO 2005/097025, US 2007/156108, US 2008/0125735, and WO 2008/155722 A2, which explicitly forms part of the present disclosure.

Construction Example of Embodiment 11

The fluid-absorbent core consists of a double-layered high-loaded single core system each layer having a uniform rectangular size. The layered fluid-absorbent core between (A) and (B) comprises a double-layered system of hydrophilic fibers (synthetic fibers), each layer having a rectangular size. The fluid-absorbent core is encapsulated by wrapping with a spunbond material having a basis weight of 10 gsm. The density of the fluid-absorbent core is for the font overall average 0.20 g/cm$^3$, for the insult zone 0.20 g/cm$^3$, for the back overall average 0.21 g/cm$^3$. The basis weight of the fluid-absorbent core is for the front overall average 551.51 gsm, for the insult zone 585.71 gsm, for the back overall average 569.63 gsm. The thickness of the fluid-absorbent core has an average of 2.9 mm.

The fluid-absorbent core holds 81.6% by weight distributed fluid-absorbent polymer particles, the quantity of fluid-absorbent polymer particles within the fluid-absorbent core is 12.9 g.

The fluid-absorbent polymer particles derived from dropletization polymerization as described in WO 2008/009580 A1, table 1, example 5, exhibiting the following features and absorption profile:
CRC of 28.7 g/g
SFC of $51\times10^{-7}$ cm$^3$ s/g
AUHL of 24.5 g/g
AUL of 30.3 g/g
Extractables of 2.6 wt. %
Residual monomers of 250 ppm
Moisture content of 1.6 wt. %
FSR 0.51 g/gs
PSD of 200 to 600 μm
Anticaking of 3

The fluid-absorbent polymer particles were remoisturized to a moisture content of 13% by weight.
Dimension of the fluid-absorbent core: length: 40.8 cm; front width: 14.2 cm; crotch width: 14.5 cm; rear width: 14.1 cm.

An air through bonded acquisition-distribution layer between (A) and (C) having a basis weight of 35.7 gsm is rectangular shaped and smaller than the fluid-absorbent core having a size of 24.0 cm×9.2 cm.

The fluid-absorbent article further comprises:
flat rubber elastics; elastics from spandex type fibers: 5 cuff elastics
leg cuffs from synthetic fibers showing the layer combination SMS and having a basis weight of between 13 to 17 gsm and a height of 4.7 cm
wetness indicator at the lower side of the liquid-impervious layer (B)
Dimension of the fluid-absorbent article: length: 47.9 cm; front width: 31.3 cm; crotch width: 15.4 cm; rear width: 31.3 cm Embodiment 12

A further preferred embodiment of the present invention is described in Embodiment 12 (pantiliner) hereinafter. Thus, a preferred fluid-absorbent article comprising (A) an upper liquid-pervious layer comprising a thermo-bond layer (coverstock);
(B) a lower liquid-impervious layer comprising a composite of breathable polyethylene film and spunbond non-woven;
(C) a high-loaded single fluid-absorbent core between (A) and (B) comprising between 55 to 95% by weight fluid-absorbent polymer particles based on the total absorbent core weight and including a fluid-storage section comprising a high-loaded mixed fluid-absorbent layer wrapped with a homogenous layer of hydrophilic synthetic fibers; said high-loaded fluid-absorbent layer comprises fluid-absorbent polymer particles; suitable fluid-absorbent polymer particles for such construction having a saline flow conductivity (SFC) from about 50 to $150\times10^{-7}$ cm$^2$ s/g; said homogenous wrapping of hydrophilic synthetic fibers contains about 95% of the total fluff amount; and
(D) an air through bonded acquisition-distribution layer between (A) and (C) having a basis weight of 40 to 80 gsm; the acquisition-distribution layer is rectangular shaped and smaller than the primary fluid-absorbent core having a size of about 150 to about 250 cm$^2$.

The construction of the products chassis and the components contained therein is made and controlled by the discrete application of hotmelt adhesives as known to people skilled in the art. Examples would be e.g. Dispomelt 505B, Dispomelt Cool 1101, as well as other specific function adhesives manufactured by National Starch or Henkel.

Ultra-thin high-loaded fluid-absorbent layers can be formed by immobilization of fluid-absorbent polymer particles on a non-woven sheet using hotmelt adhesives. Preferably the fluid-absorbent polymer particles form longitudinal strips or discrete spots. Other patterns of the fluid-absorbent polymer particles are also possible.

In a preferred embodiment the ultra-thin high-loaded fluid-absorbent layers comprise at least two sheets comprising immobilized fluid-absorbent polymer particles.

Examples of ultra-thin high-loaded fluid-absorbent layers are described in EP 1 293 187 A1, U.S. Pat. No. 6,972,011, EP 1 447 066 A1, EP 1 447 067 A1, EP 1 609 448 A1, JP 2004/313580, US 2005/0137085, US 2006/0004336, US 2007/0135785 WO 2008/155699 A1, WO 2008/155701 A2, WO 2008/155702 A1, WO 2008/155710 A1, WO 2008/155711 A1, WO 2004/071363 A1, US 2003/0181115, WO 2005/097025, US 2007/156108, US 2008/0125735, and WO 2008/155722 A2, which explicitly forms part of the present disclosure.

Construction Example of Embodiment 12

The fluid-absorbent core consists of a high-loaded single core system having a uniform rectangular size. The fluid-absorbent core between (A) and (B) comprises a fluid-storage section comprising a high-loaded fluid-absorbent layer wrapped in a homogenous layer of hydrophilic synthetic fibers. The fluid-absorbent core is encapsulated by wrapping it both in a C-wrap and a full wrap configuration with a spunbond material having a basis weight of 10 gsm. The density of the fluid-absorbent core is for the font overall average 0.16 g/cm$^3$, for the insult zone 0.25 g/cm$^3$, for the back overall average 0.19 g/cm$^3$. The basis weight of the fluid-absorbent core is for the front overall average 436.86 gsm, for the insult zone 707.74 gsm, for the back overall average 555.73 gsm. The thickness of the fluid-absorbent core has an average of 3.0 mm.

The fluid-absorbent core holds 80.3% by weight distributed fluid-absorbent polymer particles, the quantity of fluid-absorbent polymer particles within the fluid-absorbent core is 11.8 g.

The fluid-absorbent polymer particles derived from dropletization polymerization as described in WO 2008/009598 A1, example 7, exhibiting the following features and absorption profile:
CRC of 20.9 g/g
SFC of $149 \times 10^{-7}$ cm³ s/g
AUHL of 18.8 g/g
AUL of 22.3 g/g
Extractables of 1.6 wt. %
Residual monomers of 330 ppm
Moisture content of 16.6 wt. %
FSR 0.28 g/gs
PSD of 200 to 600 μm
Anticaking of 3

Dimension of the fluid-absorbent core: length: 40.8 cm; front width: 14.2 cm; crotch width: 14.5 cm; rear width: 14.1 cm.

An air through bonded acquisition-distribution layer between (A) and (C) having a basis weight of 35.7 gsm is rectangular shaped and smaller than the fluid-absorbent core having a size of 24.0 cm×9.2 cm.

The fluid-absorbent article further comprises:
flat rubber elastics; elastics from spandex type fibers: 5 cuff elastics
leg cuffs from synthetic fibers showing the layer combination SMS and having a basis weight of between 13 to 17 gsm and a height of 4.7 cm For improving the fit of the fluid-absorbent article, the stretchable pant of embodiment 12 provides elastics from spandex type fibers.

Dimension of the fluid-absorbent article: length: 47.9 cm; front width: 31.3 cm; crotch width: 15.4 cm; rear width: 31.3 cm.

Embodiment 13

A further preferred embodiment of the present invention is described in Embodiment 13 hereinafter. Thus, a preferred fluid-absorbent article comprising
(A) an upper liquid-pervious layer comprising a spun-bonded layer (coverstock);
(B) a lower liquid-impervious layer comprising a composite of breathable polyethylene film and spunbond non-woven;
(C) a high-loaded single fluid-absorbent core between (A) and (B) comprising between 55 to 95% by weight fluid-absorbent polymer particles based on the total absorbent core weight including a fluid-storage section comprising a high-loaded fluid-absorbent layer wrapped with a spunbond material; said high-loaded fluid-absorbent layer comprises fluid-absorbent polymer particles; suitable fluid-absorbent polymer particles for such construction having a saline flow conductivity (SFC) from about 50 to $150 \times 10^{-7}$ cm³ s/g; said homogenous wrapping of spunbond material contains about 100% of the total fluff amount; and
(D) a system of two acquisition-distribution layers between (A) and (C), comprising an upper resin bonded layer having a basis weight of 40 to 80 gsm; the upper acquisition-distribution layer is rectangular shaped having a size of about 150 to about 250 cm²; the lower acquisition-distribution layer comprising of synthetic fibers having a basis weight of 40 to 80 gsm and a size of about 100 to about 300 cm²; the upper acquisition-distribution layer is smaller than the lower acquisition-distribution layer; both acquisition-distribution layers are smaller than the fluid-absorbent core.

The construction of the products chassis and the components contained therein is made and controlled by the discrete application of hotmelt adhesives as known to people skilled in the art. Examples would be e.g. Dispomelt 505B, Dispomelt Cool 1101, as well as other specific function adhesives manufactured by National Starch or Henkel.

Ultra-thin high-loaded fluid-absorbent layers can be formed by immobilization of fluid-absorbent polymer particles on a non-woven sheet using hotmelt adhesives. Preferably the fluid-absorbent polymer particles form longitudinal strips or discrete spots. Other patterns of the fluid-absorbent polymer particles are also possible.

In a preferred embodiment the ultra-thin high-loaded fluid-absorbent layers comprise at least two sheets comprising immobilized fluid-absorbent polymer particles.

Examples of ultra-thin high-loaded fluid-absorbent layers are described in EP 1 293 187 A1, U.S. Pat. No. 6,972,011, EF 1 447 066 A1, EP 1 447 067 A1, EP 1 609 448 A1, JP 2004/313580, US 2005/0137085, US 2006/0004336, US 2007/0135785 WO 2008/155699 A1, WO 2008/155701 A2, WO 2008/155702 A1, WO 2008/155710 A1, WO 2008/155711 A1, WO 2004/071363 A1, US 2003/0181115, WO 2005/097025, US 2007/156108, US 2008/0125735, and WO 2008/155722 A2, which explicitly forms part of the present disclosure.

Construction Example of Embodiment 13

The fluid-absorbent core consists of a high-loaded mixed single core system having an almost uniform rectangular size. The fluid-absorbent core between (A) and (B) comprises a fluid-storage section comprising a high-loaded fluid-absorbent layer wrapped in a homogenous layer of hydrophilic spunbond fibers having a basis weight of 10 gsm. The density of the fluid-absorbent core is for the front overall average 0.20 g/cm³, for the insult zone 0.19 g/cm³, for the back overall average 0.19 g/cm³. The basis weight of the fluid-absorbent core is for the front overall average 1114 gsm, for the insult zone 1007 gsm, for the back overall average 658 gsm. The thickness of the fluid-absorbent core has an average of 4.5 mm.

The fluid-absorbent layer holds 67.2% by weight distributed fluid-absorbent polymer particles, the quantity of fluid-absorbent polymer particles within the fluid-absorbent core is 14.1 g.

The fluid-absorbent polymer particles derived from dropletization polymerization as described in WO 2008/009580 A1, table 1, example 5, exhibiting the following features and absorption profile:
CRC of 28.7 g/g
SFC of $51 \times 10^{-7}$ cm³ s/g
AUHL of 24.4 g/g
AUL of 30.3 g/g
Extractables of 2.6 wt. %
Residual monomers of 250 ppm
Moisture content of 1.6 wt. %
FSR 0.51 g/gs
PSD of 200 to 600 μm
Anticaking of 3

The fluid-absorbent polymer particles were remoisturized to a moisture content of 13% by weight.

Dimension of the fluid-absorbent core: length: 43.0 cm; front width: 11.5 cm; crotch width: 7.2 cm; rear width: 12.1 cm.

The upper air through bonded acquisition-distribution layer between (A) and the lower acquisition-distribution layer having a basis weight of 65.7 gsm is rectangular shaped with dimensions of 24.9 cm×7 cm. The lower air through bonded acquisition-distribution layer between the upper acquisition-distribution layer and (C) is rectangular shaped with dimensions of 24.9 cm×7.5 cm. Both acquisition-distribution layers are smaller than the fluid-absorbent core.

The fluid-absorbent article further comprises:
flat rubber elastics; elastics from spandex type fibers: 3 leg elastics and 2 cuff elastics
leg cuffs from synthetic fibers showing the layer combination SMS and having a basis weight of between 13 to 17 gsm and a height of 3.4 cm
mechanical closure system with landing zone of dimension 14.9 cm×3.8 cm and adhesive closure tapes of 3.0 cm×1.3 cm; attached to hook fastening tape of 3.0 cm×1.3 cm Dimension of the fluid-absorbent article: length: 50.9 cm; front width: 24.5 cm; crotch width: 24.3 cm; rear width: 24.5 cm.

Embodiment 14

A further preferred embodiment of the present invention is described in Embodiment 14 hereinafter. Thus, a preferred fluid-absorbent article comprising (A) an upper liquid-pervious layer comprising a spun-bonded layer (coverstock);
(B) a lower liquid-impervious layer comprising a composite of breathable polyethylene film and spunbond nonwoven;
(C) a high-loaded single fluid-absorbent core between (A) and (B) comprising between 55 to 95% by weight fluid-absorbent polymer particles based on the total absorbent core weight including a fluid-storage section comprising a high-loaded fluid-absorbent layer wrapped with a spunbond material; said high-loaded fluid-absorbent layer comprises fluid-absorbent polymer particles; suitable fluid-absorbent polymer particles for such construction having a saline flow conductivity (SFC) from about 50 to 150×10$^{-7}$ cm$^3$ s/g; said homogenous wrapping of spunbond material contains about 100% of the total fluff amount; and
(D) a system of two acquisition-distribution layers between (A) and (C), comprising an upper resin bonded layer having a basis weight of 40 to 80 gsm; the upper acquisition-distribution layer is rectangular shaped having a size of about 150 to about 250 cm$^2$; the lower acquisition-distribution layer comprising of synthetic fibers having a basis weight of 40 to 80 gsm and a size of about 100 to about 300 cm$^2$; the upper acquisition-distribution layer is smaller than the lower acquisition-distribution layer; both acquisition-distribution layers are smaller than the fluid-absorbent core;

The construction of the products chassis and the components contained therein is made and controlled by the discrete application of hotmelt adhesives as known to people skilled in the art. Examples would be e.g. Dispomelt 505B, Dispomelt Cool 1101, as well as other specific function adhesives manufactured by National Starch or Henkel.

Ultra-thin high-loaded fluid-absorbent layers can be formed by immobilization of fluid-absorbent polymer particles on a non-woven sheet using hotmelt adhesives. Preferably the fluid-absorbent polymer particles form longitudinal strips or discrete spots. Other patterns of the fluid-absorbent polymer particles are also possible.

In a preferred embodiment the ultra-thin high-loaded fluid-absorbent layers comprise at least two sheets comprising immobilized fluid-absorbent polymer particles.

Examples of ultra-thin high-loaded fluid-absorbent layers are described in EP 1 293 187 A1, U.S. Pat. No. 6,972,011, EF 1 447 066 A1, EP 1 447 067 A1, EP 1 609 448 A1, JP 2004/313580, US 2005/0137085, US 2006/0004336, US 2007/0135785 WO 2008/155699 A1, WO 2008/155701 A2, WO 2008/155702 A1, WO 2008/155710 A1, WO 2008/155711 A1, WO 2004/071363 A1, US 2003/0181115, WO 2005/097025, US 2007/156108, US 2008/0125735, and WO 2008/155722 A2, which explicitly forms part of the present disclosure.

Construction Example of Embodiment 14

The fluid-absorbent core consists of a high-loaded mixed single core system having an almost uniform rectangular size. The fluid-absorbent core between (A) and (B) comprises a fluid-storage section comprising a high-loaded fluid-absorbent layer wrapped in a homogenous layer of hydrophilic spunbond fibers having a basis weight of 10 gsm. The density of the fluid-absorbent core is for the front overall average 0.25 g/cm$^3$, for the insult zone 0.25 g/cm$^3$, for the back overall average 0.26 g/cm$^3$. The basis weight of the fluid-absorbent core is for the front overall average 878.70 gsm, for the insult zone 1237.56 gsm, for the back overall average 495.60 gsm. The thickness of the fluid-absorbent core has an average of 3.1 mm.

The fluid-absorbent layer holds 100% by weight distributed fluid-absorbent polymer particles, the quantity of fluid-absorbent polymer particles within the fluid-absorbent core is 14.14 g.

The fluid-absorbent polymer particles derived from dropletization polymerization as described in WO 2008/009580 A1, table 2, example 6, exhibiting the following features and absorption profile:
CRC of 27.7 g/g
SFC of 65×10$^{-7}$ cm$^3$ s/g
AUHL of 23.4 g/g
AUL of 28.9 g/g
Extractables of 3.3 wt. %
Residual monomers of 280 ppm
Moisture content of 1.2 wt. %
FSR 0.34 g/gs
PSD of 200 to 600 μm
Anticaking of 3

The fluid-absorbent polymer particles were remoisturized to a moisture content of 13% by weight.

Dimension of the fluid-absorbent core: length: 42.4 cm; front width: 10.6 cm; crotch width: 10.2 cm; rear width: 10.5 cm.

The upper air through bonded acquisition-distribution layer between (A) and the lower acquisition-distribution layer having a basis weight of 58.8 gsm is rectangular shaped with dimensions of 24.7 cm×7.3 cm. The lower air through bonded acquisition-distribution layer between the upper acquisition-distribution layer and (C) is rectangular shaped with dimensions of 20.3 cm×8.2 cm. Both acquisition-distribution layers are smaller than the fluid-absorbent core.

The fluid-absorbent article further comprises:
flat rubber elastics; elastics from spandex type fibers: 2 leg elastics and 2 cuff elastics leg cuffs from synthetic fibers showing the layer combination SMS and having a basis weight of between 13 to 17 gsm and a height of 4.4 cm waistband: front 13.7 cm×2.1 cm; rear: 14.8 cm×2.2 cm Dimension of the fluid-absorbent article: length: 46.7 cm; front width: 33.5 cm; crotch width: 16.0 cm; rear width: 33.5 cm.

The fluid-absorbent polymer particles and the fluid-absorbent articles are tested by means of the test methods described below.

Methods:

The measurements should, unless stated otherwise, be carried out at an ambient temperature of 23±2° C. and a relative atmospheric humidity of 50±10%. The fluid-absorbent polymers are mixed thoroughly before the measurement.

Rewet Value

This test consists of multiple insults of 0.9 wt. % NaCl solution in deionized water. The rewet is measured by the amount of fluid the article released under pressure. The rewet is measured after each insult.

The article is clamped nonwoven side up onto the inspection table. The insult point is marked on the article accordingly with regard to the type and gender of the diaper to be tested (i.e. in the centre of the fluid-absorbent core for girl, 2.5 cm towards the front for unisex and 5 cm towards the front for boy). A separatory funnel is positioned above the article so that the spout is 2 cm away from the surface and directly above the marked insult point.

For the primary insult 100 g of NaCl solution is placed into the separation funnel. The NaCl solution is released with a flow rate of 7±1 g/s. Next, the fluid is allowed to be absorbed by the article for 10 minutes. After the 10 minutes have elapsed, 10 filter papers (Whatman® No. 1; 9 cm diameter) are placed over the insult point, this value is the dry weight (D1). On top of the filter papers, a 2.5 kg circular weight (8 cm diameter) is added. After 2 minutes, the filter papers are re-weighed, this value is the wet weight (V/1).

The rewet is calculated as follows:

$$\text{Rewet Value [g]} = W1 - D1$$

For the rewet of the secondary insult the procedure for the primary insult is repeated. 50 g of NaCl solution and 20 filter papers are used.

For the rewet of the tertiary and following insults the procedure for the primary insult is repeated. 50 g of NaCl solution and 30 filter papers are used.

Rewet Under Load/Acquisition Time

This test determines acquisition time and the amount of fluid a fluid-absorbent article releases after being maintained under pressure following multiple separate insults. The rewet under load is measured by the amount of fluid the article released under pressure. The rewet under load and the acquisition time are measured after each insult.

The article is clamped nonwoven side up onto the inspection table. The insult point is marked on the article accordingly with regard to the type and gender of the diaper to be tested (i.e. in the centre of the fluid-absorbent core for girl, 2.5 cm towards the front for unisex and 5 cm towards the front for boy). A 3.64 kg circular weight (10 cm diameter) having a central opening (2.3 cm diameter) is placed with the opening on the previously marked insult point. A perspex tube is positioned in the central opening.

For the primary insult 100 g of 0.9 wt. % NaCl solution is poured into the perspex tube in one shot. The amount of time in seconds for the fluid to be fully absorbed into the article is recorded as acquisition time. After 10 minutes have elapsed from the time of liquid addition, 10 filter papers (Whatman® No. 1; 9 cm diameter) are placed over the insult point, this value is the dry weight (W1). On top of the filter papers, a 2.5 kg circular weight (8 cm diameter) is added. After 2 minutes, the filter papers are reweighed, this value is the wet weight (W2).

The rewet under load is calculated as follows:

$$\text{Rewet Under Load [g]} = W2 - W1$$

For the rewet under load of the secondary insult the procedure for the primary insult's repeated. 50 g of NaCl solution and 20 filter papers are used.

For the rewet under load of the tertiary and following insults the procedure for the primary insult is repeated. 50 g of NaCl solution and 30 filter papers are used.

Density of the Fluid-Absorbent Core

This test determines the density of the fluid-absorbent core in the point of interest.

The fluid-absorbent article is clamped nonwoven side up onto the inspection table. The insult point is marked on the article accordingly with regard to the type and gender of the diaper to be tested (i.e. in the centre of the fluid-absorbent core for girl, 2.5 cm towards the front for unisex and 5 cm towards the front for boy).

Next, a 6 cm×core width section is marked on the fluid-absorbent core with the point of interest in the centre of the section. Three readings of thickness of the section are taken using a Portable Thickness Gauge Model J100 (SDL Atlas, Inc.; Stockport; UK) and the average is recorded (T). The section of the fluid-absorbent core is cut out of and the weight of the cut out section is recorded (WT).

The density of the fluid-absorbent core is calculated as follows:

$$\text{Density [g/cm}^3\text{]} = WT/(36 \text{ cm}^2 \times T)$$

Saline Flow Conductivity (SFC)

The saline flow conductivity is, as described in EP 0 640 330 A1, determined as the gel layer permeability of a swollen gel layer of fluid-absorbent polymer particles, although the apparatus described on page 19 and in FIG. 8 in the aforementioned patent application was modified to the effect that the glass frit (40) is no longer used, the plunger (39) consists of the same polymer material as the cylinder (37) and now comprises 21 bores having a diameter of 9.65 mm each distributed uniformly over the entire contact surface. The procedure and the evaluation of the measurement remains unchanged from EP 0 640 330 A1. The flow rate is recorded automatically.

The saline flow conductivity (SFC) is calculated as follows:

$$SFC \text{ [cm}^3\text{s/g]} = (Fg(t=0) \times L0)/(d \times A \times WP),$$

where $Fg(t=0)$ is the flow rate of NaCl solution in g/s, which is obtained by means of a linear regression analysis of the $Fg(t)$ data of the flow determinations by extrapolation to $t=0$, L0 is the thickness of the gel layer in cm, d is the density of the NaCl solution in g/cm$^3$, A is the surface area of the gel layer in cm$^2$ and WP is the hydrostatic pressure over the gel layer in dyn/cm$^2$.

Free Swell Rate (FSR)

1.00 g (~W1) of the dry fluid-absorbent polymer particles is weighed into a 25 ml glass beaker and is uniformly distributed on the base of the glass beaker. 20 ml of a 0.9% by weight sodium chloride solution are then dispensed into a second glass beaker, the content of this beaker is rapidly added to the first beaker and a stopwatch is started. As soon as the last drop of salt solution is absorbed, confirmed by the disappearance of the reflection on the liquid surface, the stopwatch is stopped. The exact amount of liquid poured from the second beaker and absorbed by the polymer in the first beaker is accurately determined by weighing back the second beaker (=W2). The time needed for the absorption, which was measured with the stopwatch, is denoted t. The disappearance of the last drop of liquid on the surface is defined as time t.

The free swell rate (FSR) is calculated as follows:

$$FSR\ [g/gs]=W2/(W1\times t)$$

When the moisture content of the hydrogel-forming polymer is more than 3% by weight, however, the weight W1 must be corrected for this moisture content.

Water Vapor Transmission Rate (WVTR)

The water vapor transmission rate (WVTR) is determined according to the test method written in U.S. Pat. No. 6,217,890, column 32, lines 15 to 56.

Anticaking

The anticaking is determined according to the test method written in WO 2005/097881 A1, page 19, lines 14 to 24. For quantitative ranking grades are given between 1 and 5, whereby grade 1 does not leave any residue in the beaker and at grade 5 no material can be poured out of the beaker.

Residual Monomers

The level of residual monomers in the fluid-absorbent polymer particles is determined by the EDANA recommended test method No. WSP 410.2-05 "Residual Monomers".

Particle Size Distribution

The particle size distribution of the fluid-absorbent polymer particles is determined by the EDANA recommended test method No. WSP 420.2-05 "Particle Size Distribution". For determination of the medium particle size the proportions by mass of the screen fractions are plotted in cumulated form and the mean particle size is determined graphically. The mean particle size here is the value of the mesh size which gives rise to a cumulative 50% by weight.

Moisture Content

The moisture content of the fluid-absorbent polymer particles is determined by the EDANA recommended test method No. WSP 430.2-05 "Moisture Content".

Centrifuge Retention Capacity (CRC)

The centrifuge retention capacity of the fluid-absorbent polymer particles is determined by the EDANA recommended test method No. WSP 441.2-05 "Centrifuge Retention Capacity", wherein for higher values of the centrifuge retention capacity lager tea bags have to be used.

Absorbency Under Load (AUL)

The absorbency under load of the fluid-absorbent polymer particles is determined by the EDANA recommended test method No. WSP 442.2-05 "Absorption Under Pressure"

Absorbency Under High Load (AUHL)

The absorbency under high load of the fluid-absorbent polymer particles is determined analogously to the EDANA recommended test method No. WSP 442.2-05 "Absorption Under Pressure", except using a weight of 49.2 g/cm² instead of a weight of 21.0 g/cm².

Extractables

The level of extractable constituents in the fluid-absorbent polymer particles is determined by the EDANA recommended test method No. WSP 470.2-05 "Extractables".

The EDANA test methods are obtainable, for example, from the EDANA, Avenue Eugène Plasky 157, B-1030 Brussels, Belgium.

EXAMPLES

Example 1

The fluid-absorbent polymer particles were produced as follows:

2.064 kg/h of acrylic acid and 18.476 kg/h of sodium acrylate (37.5% by weight solution in water) were mixed with 12.53 g/h of 3-tuply ethoxylated glycerol triacrylate (approx. 85% strength by weight). The resulting mixture was dropletized in a heated dropletization tower filled with a nitrogen atmosphere (height 12 m, width 2 m, gas velocity 0.1 m/s in concurrent). The metering rate of the mixture was 20.5 kg/h. The dropletizer plate had 30×200 μm bores. The initiator was metered into the monomer solution upstream of the dropletizer by means of a static mixer. The initiators used were 0.67 kg/h of a 5.5% by weight solution of 2,2'-azobis[2-(2-imidazolin-2-yl)propane]dihydrochloride in water and 0.614 kg/h of a 3% by weight solution of sodium peroxodisulfate in water. The heating output of the gas preheating was controlled such that the gas outlet temperature in the dropletization tower was a constant 130° C.

The resulting polymer particles had a moisture content of 15.8% by weight.

Charges of 100 kg polymer particles were placed in a 200 l drum and mixed for 2 hours and 21 rpm using a drum hoop mixer (type RRM 200; J. Engelsmann A G, Ludwigshafen; Germany) with 0.08% by weight of Sipernat® D17 (Evonik Degussa GmbH; Frankfurt; Germany).

The resulting coated polymer particles were thermally aftertreated in a fluidized bed. To this end, an air/steam mixture was flowed toward the polymers from below for 80 minutes. The gas velocity was 0.8 m/s. The gas temperature was 80 to 90° C. The relative moisture content of the gas stream was 25 to 35%. The gas stream comprised 0.12 to 0.15 kg of steam per kg of dry gas.

The aftertreated polymer particles had a moisture content of 13.0% by weight, a centrifuge retention capacity (CRC) of 31.6 g/g, an absorption under high load (AUHL) of 16.2 g/g, a free swell rate (FSR) of 1.02 g/gs, a mean sphericity of 0.94 and a saline flow conductivity (SFC) of $6\times10^{-7}$ cm³ s/g.

Example 2

Fluid-Absorbent Core Consisting of 50 wt. % Fluid-Absorbent Polymer Particles and 50 Wt. % Cellulose Fluff Six portions of 0.83±0.0019 were weighed out of 5.0 g fluid-absorbent polymer particles on weighing boats.

5.0 g of cellulose fluff with an addition of 0.5 g were weighed out in a weighing pan and divided into six equal portions of 0.92±0.01 g.

The fluid-absorbent core was produced as follows:

A fleece tissue was placed on a rectangular wire mesh, 17.5 cm in length and 11 cm in width, so that the fleece tissue covers the wire mesh. The wire mesh was placed underneath a perpendicular shaft of the same size, where a longitudinally installed brush rotates about 68 cm above the wire mesh. At the end, 10 cm above the wire mesh, the perpendicular shaft was reduced until an inner area 16 cm in length and 9 cm in width. The brush was 17.5 cm in length and 10 cm in diameter and rotates at 13.5 revolutions per second. Vacuum was sitting underneath the wire mesh that contains the fleece tissue.

The first portion of cellulose fluff was added downwardly to the rotating brush. After 30 seconds, the first portion of polymer was put downwardly onto the rotating brush.

The additions of cellulose fluff and fluid-absorbent polymer particles were repeated in total two more times after every 30 seconds. The wire mesh with the tissue was then turned horizontally about 180°.

The additions of cellulose fluff and fluid-absorbent polymer particles were then repeated three more times altogether.

The fluid-absorbent core was removed from the fleece tissue in such a way that it was turned over very carefully on one layer of paper tissue.

A card was used to remove the adhering particles from the fleece tissue. Then, the paper tissue (e.g. Tork® Universal Wiper 320; SCA Tissue Europe), 33.8 cm in length and 23.4 cm in width was folded around the water-absorbing composite. The resulting water-absorbing composite was compressed by a compactor (type Polystat 200T; Ruth Schwabenthan Maschinenfabrik; Berlin; Germany) 15 sec at a setting of 50 bar. Then the paper tissue was opened again and folded. And the water-absorbing composite was now turned horizontally about 180° and compressed again 15 sec at a setting of 50 bar.

Acquisition time and rewet value of the core were determined. The results are summarized in Table 1 and 2.

Examples 3 and 4

Comparative

The procedure of Example 2 was repeated. The fluid-absorbent polymer particles of Example 1 were replaced by HySorb® R7061 and HySorb® R7057 (BASF SE; Ludwigshafen; Germany). HySorb® R7061 and HySorb® R7057 consist of irregular shaped fluid-absorbent polymer particles produced by gel polymerization.

HySorb® R7061 had a moisture content of 1.0% by weight, a centrifuge retention capacity (CRC) of 32.0 g/g, an absorption under high load (AUHL) of 23.0 g/g, a free swell rate (FSR) of 0.27 g/gs and a saline flow conductivity (SFC) of $23 \times 10^{-7}$ cm$^3$ s/g.

HySorb® R7057 had a moisture content of 0.8% by weight, a centrifuge retention capacity (CRC) of 36.7 g/g, an absorption under high load (AUHL) of 16.1 g/g, a free swell rate (FSR) of 0.30 gigs and a Saline Flow Conductivity (SFC) of $3 \times 10^{-7}$ cm$^3$ s/g.

Acquisition time and rewet value of the cores were determined. The results are summarized in Table 1 and 2.

Example 5

The fluid-absorbent core (C) was produced as follows:

The procedure of Example 2 was repeated. 4.5 g of fluid-absorbent polymer particles from Example 1 were used instead of 5.0 g.

The acquisition distribution layer (D) was produced as follows:

The procedure of Example 2 was repeated. 0.5 g of fluid-absorbent polymer particles from Example 1 were used instead of 5.0 g.

The fluid-absorbent core and the acquisition distribution layer were combined to a composite. Acquisition time and rewet value of the composite were determined. The results are summarized in Table 1 and 2.

Examples 6 and 7

Comparative

The procedure of Example 5 was repeated. The fluid-absorbent polymer particles of Example 1 were replaced by HySorb® R7061 and HySorb® R7057 (BASF SE; Ludwigshafen; Germany).

The fluid-absorbent core and the acquisition distribution layer were combined to a composite. Acquisition time and rewet value of the composite were determined. The results are summarized in Table 1 and 2.

TABLE 1

Acquisition time

| Example | 1$^{st}$ insult | 2$^{nd}$ insult | 3$^{rd}$ insult | 4$^{th}$ insult |
|---------|-----------------|-----------------|-----------------|-----------------|
| 2       | 26 s            | 29 s            | 34 s            | 42 s            |
| 3*)     | 19 s            | 9 s             | 8 s             | 10 s            |
| 4*)     | 20 s            | 12 s            | 12 s            | 14 s            |
| 5       | 22 s            | 20 s            | 22 s            | 27 s            |
| 6*)     | 18 s            | 12 s            | 12 s            | 16 s            |
| 7*)     | 16 s            | 12 s            | 12 s            | 15 s            |

*)comparative

TABLE 2

Rewet value

| Example | 1$^{st}$ insult | 2$^{nd}$ insult | 3$^{rd}$ insult | 4$^{th}$ insult |
|---------|-----------------|-----------------|-----------------|-----------------|
| 2       | 0.1 g           | 0.4 g           | 2.3 g           | 5.8 g           |
| 3*)     | 0.1 g           | 0.3 g           | 2.6 g           | 5.8 g           |
| 4*)     | 0.1 g           | 0.2 g           | 1.9 g           | 4.2 g           |
| 5       | 0.1 g           | 1.0 g           | 3.7 g           | 6.9 g           |
| 6*)     | 0.1 g           | 1.2 g           | 5.0 g           | 8.7 g           |
| 7*)     | 0.1 g           | 1.4 g           | 4.9 g           | 8.5 g           |

*)comparative

The examples demonstrate that acquisition time of fluid-absorbent cores, comprising hollow spherical fluid-absorbent polymer particles, can be improved without having an impact on the rewet value by using an acquisition distribution layer.

Using commercial available irregular shaped fluid-absorbent polymer particles, an acquisition distribution layer has no effect on the acquisition time and a negative impact on the rewet value.

The invention claimed is:

1. A fluid-absorbent article, comprising
   (A) an upper liquid-pervious layer,
   (B) a lower liquid-impervious layer,
   (C) a fluid-absorbent core between the layer (A) and the layer (B), comprising a fibrous material and 10 to 95% by weight of fluid-absorbent polymer particles, and
   (D) an acquisition distribution layer between the layer (A) and the core (C), comprising a fibrous material and 0 to 20% by weight of fluid-absorbent polymer particles,
   wherein the fluid-absorbent polymer particles have a mean sphericity of at least 0.84.

2. A fluid-absorbent article according to claim 1, wherein the fluid-absorbent polymer particles have a content of hydrophobic solvents of less than 0.005% by weight.

3. A fluid-absorbent article according to claim 1, wherein the fluid-absorbent polymer particles have a moisture content of at least 8% by weight.

4. A fluid-absorbent article according to claim 1, wherein the fluid-absorbent core contains at least 9 g of the fluid-absorbent polymer particles.

5. A fluid-absorbent article according to claim 1, wherein at least 90% by weight of the fluid-absorbent polymer particles have a diameter of from 100 to 800 μm.

6. A fluid-absorbent article according to claim 1, wherein the fluid-absorbent polymer particles consist at least partly of polymerized acid group-bearing monomer.

7. A fluid-absorbent article according to claim 1, wherein the fluid-absorbent polymer particles comprise to an extent of at least 0.05% by weight of a copolymerized crosslinker.

8. A fluid-absorbent article according to claim 1, wherein the fibrous material is hydrophilic.

9. A fluid-absorbent article according to claim 1, wherein the fibrous material is cellulose fibers.

10. A fluid-absorbent article according to claim 1, wherein the fluid-absorbent polymer particles have a centrifuge retention capacity (CRC) of at least 10 g/g.

11. A fluid-absorbent article according to claim 1, wherein the fluid-absorbent polymer particles have a saline flow conductivity (SFC) of at least $5 \times 10^{-7}$ cm$^3$s/g.

12. A fluid-absorbent article according to claim 1, wherein the top view area of the core (C) is at least 200 cm$^2$.

13. A fluid-absorbent article according to claim 1, wherein the acquisition distribution layer (D) contains from 0.01 to 20% by weight of the fluid-absorbent polymer particles.

* * * * *